US008880193B1

(12) United States Patent
Thenuwara et al.

(10) Patent No.: US 8,880,193 B1
(45) Date of Patent: Nov. 4, 2014

(54) COCHLEAR ELECTRODE ARRAY

(75) Inventors: Chuladatta Thenuwara, Castaic, CA (US); Timothy Beerling, San Francisco, CA (US)

(73) Assignee: Advanced Bionics, LLC, Valencia, CA (US)

( * ) Notice: Subject to any disclaimer, the term of this patent is extended or adjusted under 35 U.S.C. 154(b) by 774 days.

(21) Appl. No.: 12/781,137

(22) Filed: May 17, 2010

Related U.S. Application Data

(60) Provisional application No. 61/180,737, filed on May 22, 2009.

(51) Int. Cl.
*A61N 1/05* (2006.01)
*A61N 1/36* (2006.01)

(52) U.S. Cl.
CPC .......... *A61N 1/0541* (2013.01); *A61N 1/36032* (2013.01)
USPC .................. 607/137; 607/55; 607/56; 607/57

(58) Field of Classification Search
CPC ......................... A61N 1/36032; A61N 1/0541
USPC ............................................. 607/55–57, 137
See application file for complete search history.

(56) References Cited

U.S. PATENT DOCUMENTS

| | | |
|---|---|---|
| 5,123,422 A | 6/1992 | Charvin |
| 5,437,632 A | 8/1995 | Engelson |
| 5,470,322 A | 11/1995 | Horzewski et al. |
| 5,476,497 A | 12/1995 | Mower et al. |
| 5,573,520 A | 11/1996 | Schwartz et al. |
| 5,580,699 A | 12/1996 | Layman et al. |
| 5,630,839 A | 5/1997 | Corbett et al. |
| 5,649,970 A | 7/1997 | Loeb et al. |
| 5,653,742 A | 8/1997 | Parker et al. |

(Continued)

FOREIGN PATENT DOCUMENTS

| | | |
|---|---|---|
| DE | 3718324 A1 | 6/1987 |
| EP | 1341578 B1 | 4/2002 |

(Continued)

OTHER PUBLICATIONS

He, Bo et al., Surface Texture effect on Friction of a Microtextured Polydimethylsiloxane, Tribology Letters, vol. 31, No. 3, Aug. 12, 2008; pp. 1-11.

(Continued)

*Primary Examiner* — Tammie K Heller
(74) *Attorney, Agent, or Firm* — Steven L. Nichols; Van Cott, Bagley, Cornwall & McCarthy P.C.

(57) ABSTRACT

A method for forming a cochlear electrode array with a plurality of electrodes which are spaced so as to stimulate sites within a cochlea includes shaping a sheet of electrically conductive material to form a support structure and a plurality of electrodes, in which the electrodes are tethered to the support structure at the spacing of the cochlear electrode array. A cochlear lead includes a flexible body that has frictional characteristics that vary about its circumference. A cochlear lead includes a flexible body with a first region and a second region with different surface textures. This generates differential sliding forces during insertion of the cochlear lead which influence a motion of the cochlear lead during insertion. The cochlear lead having an electrode array with varying stiffness along its length is also provided.

20 Claims, 14 Drawing Sheets

(56) References Cited

U.S. PATENT DOCUMENTS

| | | |
|---|---|---|
| 5,658,709 A | 8/1997 | Layman et al. |
| 5,762,630 A | 6/1998 | Bley et al. |
| 5,800,500 A | 9/1998 | Spelman et al. |
| 5,999,859 A | 12/1999 | Jolly |
| 6,048,338 A | 4/2000 | Larson et al. |
| 6,119,044 A | 9/2000 | Kuzma et al. |
| 6,125,302 A | 9/2000 | Kuzma |
| 6,151,526 A | 11/2000 | Tziviskos |
| 6,249,708 B1 | 6/2001 | Nelson et al. |
| 6,263,249 B1 | 7/2001 | Stewart et al. |
| 6,321,125 B1 | 11/2001 | Kuzma |
| 6,368,316 B1 | 4/2002 | Jansen et al. |
| 6,421,569 B1 | 7/2002 | Treaba et al. |
| 6,428,489 B1 | 8/2002 | Jacobsen et al. |
| 6,438,425 B1 | 8/2002 | Miller et al. |
| 6,475,209 B1 | 11/2002 | Larson et al. |
| 6,493,590 B1 | 12/2002 | Wessman |
| 6,556,873 B1 | 4/2003 | Smits |
| 6,562,021 B1 | 5/2003 | Derbin et al. |
| 6,604,283 B1 | 8/2003 | Kuzma |
| 6,757,970 B1 | 7/2004 | Kuzma et al. |
| 6,858,680 B2 | 2/2005 | Gunatillake et al. |
| 6,862,805 B1 | 3/2005 | Kuzma |
| 6,887,235 B2 | 5/2005 | O'Connor et al. |
| 6,968,238 B1 | 11/2005 | Kuzma |
| 6,999,821 B2 | 2/2006 | Jenney et al. |
| 7,047,081 B2 | 5/2006 | Kuzma |
| 7,050,858 B1 | 5/2006 | Kuzma et al. |
| 7,063,708 B2 | 6/2006 | Gibson et al. |
| 7,066,931 B2 | 6/2006 | O'Connor et al. |
| 7,115,183 B2 | 10/2006 | Larson et al. |
| 7,146,227 B2 | 12/2006 | Dadd et al. |
| 7,239,923 B1 | 7/2007 | Tockman et al. |
| 7,240,416 B2 | 7/2007 | Milojevic |
| 7,269,461 B2 | 9/2007 | Dadd et al. |
| 7,272,449 B2 | 9/2007 | Dadd et al. |
| 7,315,763 B2 | 1/2008 | Kuzma et al. |
| 7,319,906 B2 | 1/2008 | Kuzma et al. |
| 7,328,072 B2 | 2/2008 | Milojevic et al. |
| 7,389,148 B1 | 6/2008 | Morgan |
| 7,403,823 B1 | 7/2008 | Kroll et al. |
| 7,451,000 B2 | 11/2008 | Gibson et al. |
| 7,540,865 B2 | 6/2009 | Griffin et al. |
| 7,571,012 B2 | 8/2009 | Gibson |
| 7,742,827 B2 | 6/2010 | Lenarz et al. |
| 8,180,459 B2 | 5/2012 | Dadd et al. |
| 8,244,366 B2 | 8/2012 | Chang et al. |
| 2002/0029074 A1 | 3/2002 | Treaba et al. |
| 2003/0040684 A1 | 2/2003 | Soukup |
| 2003/0045921 A1 | 3/2003 | Dadd et al. |
| 2003/0093139 A1 | 5/2003 | Gibson et al. |
| 2003/0181967 A1 | 9/2003 | Dadd et al. |
| 2004/0030376 A1 | 2/2004 | Gibson et al. |
| 2004/0078057 A1 | 4/2004 | Gibson |
| 2004/0127968 A1 | 7/2004 | Kuzma et al. |
| 2005/0234535 A1 | 10/2005 | Risi et al. |
| 2006/0020318 A1 | 1/2006 | Lenarz et al. |
| 2006/0089569 A1 | 4/2006 | Soukup |
| 2006/0235500 A1 | 10/2006 | Gibson |
| 2007/0073371 A1 | 3/2007 | Dadd et al. |
| 2007/0127745 A1 | 6/2007 | Gibson et al. |
| 2007/0162098 A1 | 7/2007 | Risi |
| 2008/0027527 A1 | 1/2008 | Kuzma et al. |
| 2008/0077049 A1 | 3/2008 | Hirshman |
| 2008/0109011 A1 | 5/2008 | Thenuwara et al. |
| 2008/0269864 A1 | 10/2008 | Dadd et al. |
| 2009/0030483 A1 | 1/2009 | Risi et al. |
| 2009/0043358 A1 | 2/2009 | Dadd et al. |
| 2009/0043369 A1 | 2/2009 | Radeloff |
| 2009/0043370 A1 | 2/2009 | Gibson et al. |
| 2009/0062896 A1* | 3/2009 | Overstreet et al. ............ 607/137 |
| 2009/0165921 A1 | 7/2009 | Kaiser |
| 2009/0312769 A1 | 12/2009 | Dadd et al. |
| 2010/0057180 A1 | 3/2010 | Gibson |
| 2010/0106232 A1 | 4/2010 | Dadd et al. |
| 2010/0204768 A1 | 8/2010 | Jolly et al. |
| 2010/0287770 A1 | 11/2010 | Dadd et al. |
| 2011/0016710 A1 | 1/2011 | Dadd |

FOREIGN PATENT DOCUMENTS

| | | |
|---|---|---|
| EP | 1604626 A2 | 12/2005 |
| EP | 1604626 A3 | 12/2005 |
| EP | 1189560 B1 | 3/2006 |
| EP | 1604626 B1 | 12/2008 |
| EP | 2042137 A1 | 4/2009 |
| EP | 2209520 A1 | 7/2010 |
| WO | 9306698 | 4/1993 |
| WO | 9710784 | 3/1997 |
| WO | 0071063 | 11/2000 |
| WO | 0228474 | 4/2001 |
| WO | 0228473 | 4/2002 |
| WO | 0230507 | 4/2002 |
| WO | 0232498 | 4/2002 |
| WO | 0243623 | 6/2002 |
| WO | 02089907 A1 | 11/2002 |
| WO | 02094334 | 11/2002 |
| WO | 03049658 | 6/2003 |
| WO | 2004002570 | 1/2004 |
| WO | 2006000031 | 1/2006 |
| WO | 2007001218 | 1/2007 |
| WO | 2007027879 | 3/2007 |
| WO | 2009065127 A1 | 5/2009 |
| WO | 2009065171 A1 | 5/2009 |
| WO | 2009079704 | 7/2009 |
| WO | 2010015016 | 2/2010 |
| WO | 2010015017 | 2/2010 |
| WO | 2010091237 A2 | 8/2010 |
| WO | 2010091237 A3 | 8/2010 |

OTHER PUBLICATIONS

Stover, Timo et al., "Microstructured Cochlear implant electrodes," Subproject T1 of Collaborative Research Center 599; pp. 1-2; Feb. 7, 2011.

Lenarz, Thomas et al., "Nerve-Electrode Interface," Subproject D2 of Collaborative Research Center 599; pp. 1-2; Feb. 7, 2011.

Rebscher et al, Strategies to Improve Electrode Positioning and Safety in Cochlear Implants, IEEE Trans Biomed Eng, 46(3) 340-352, 1999.

Kha et al, Stiffness Properties of Nucleus Standard Straight and Contour Electrode Arrays, Med and Eng Phys 26 677-685, 2004.

Reuter G. et al., "Fine tuning of cochlear implant materials—cell interactions by femtosecond laser microstructuring." European Cells and Materials vol. 13. Suppl. 3, 2007 (p. 10).

* cited by examiner

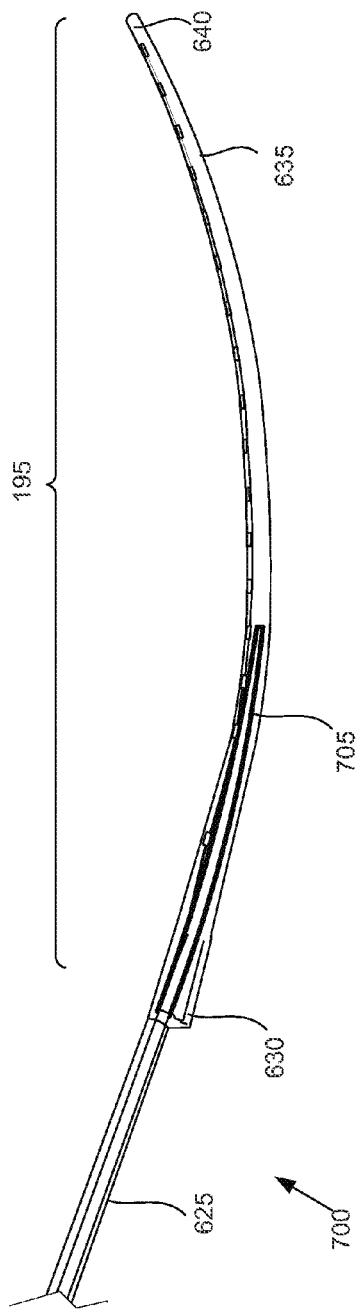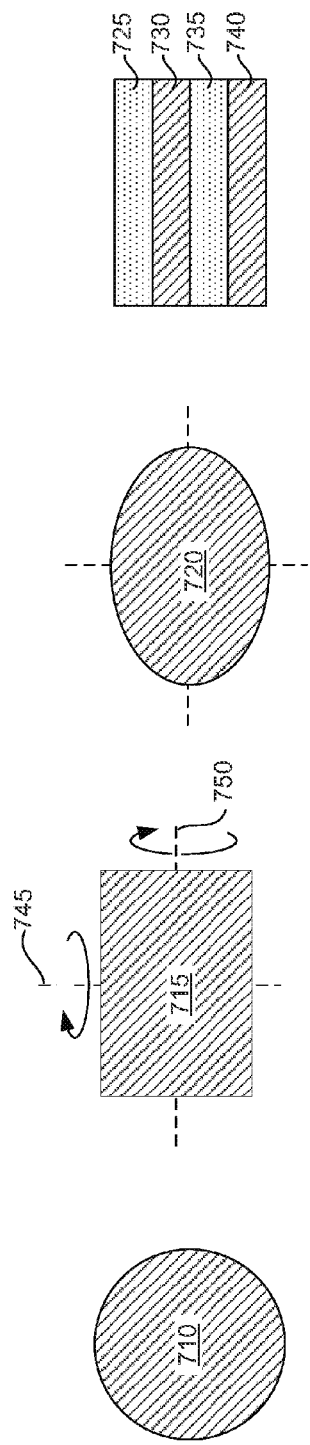

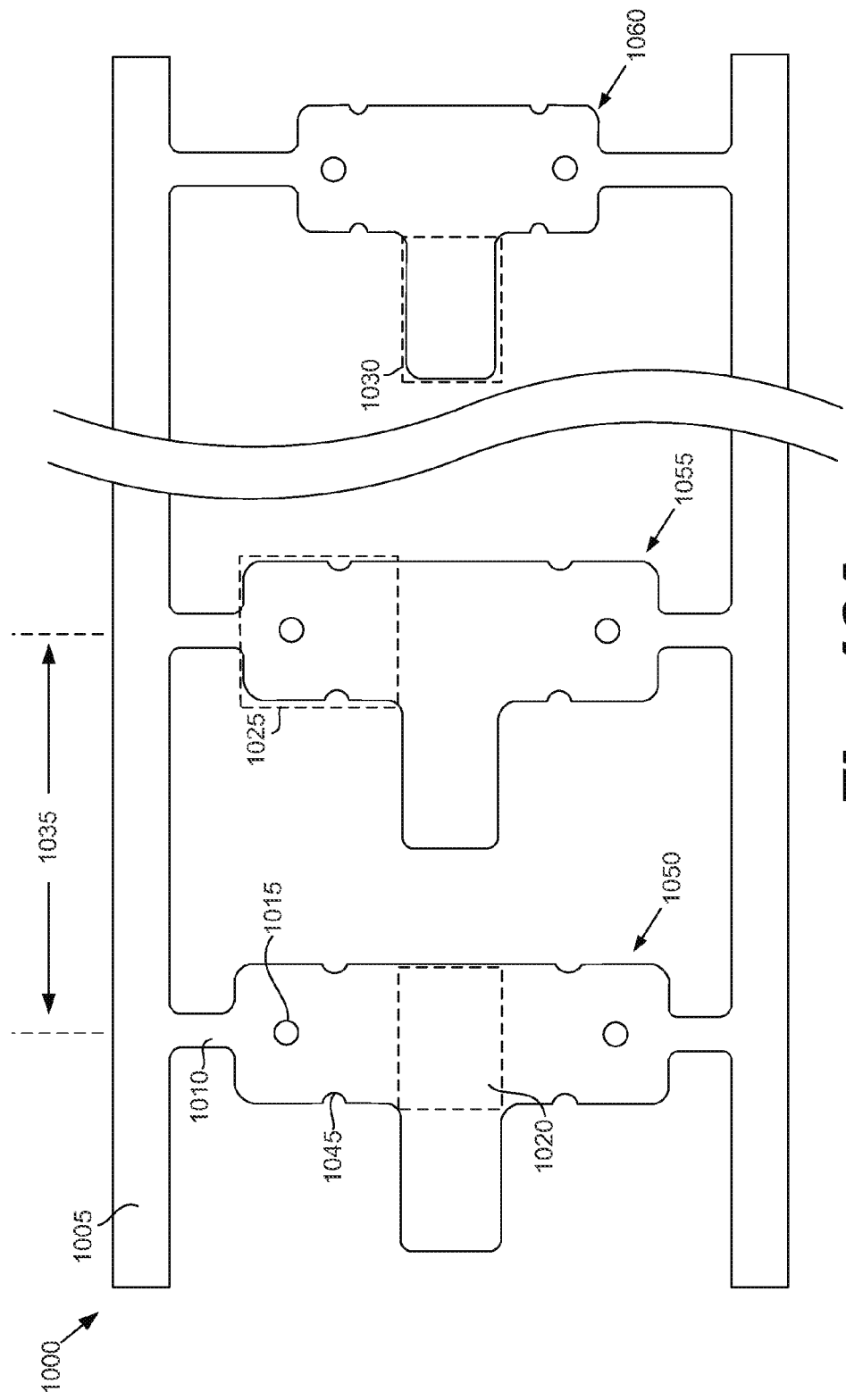

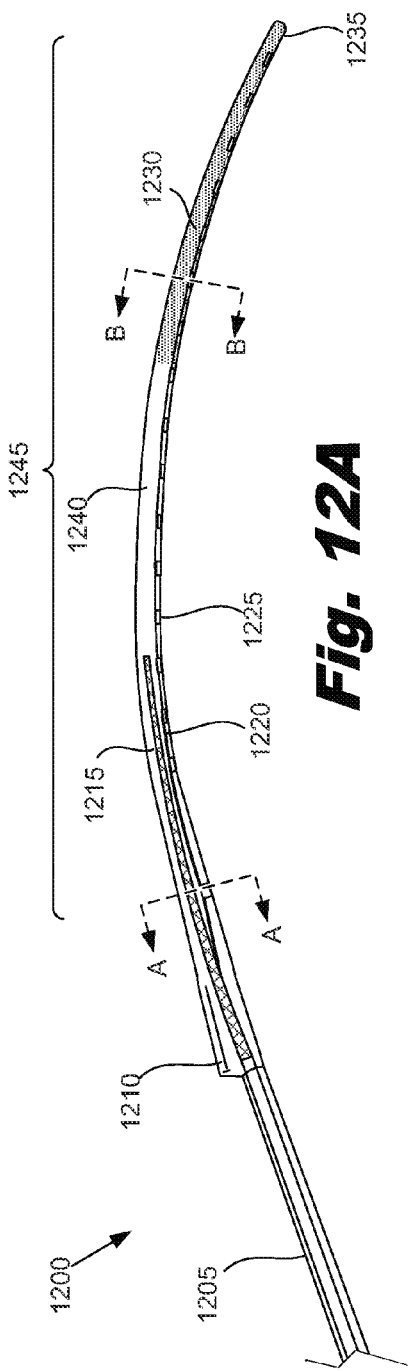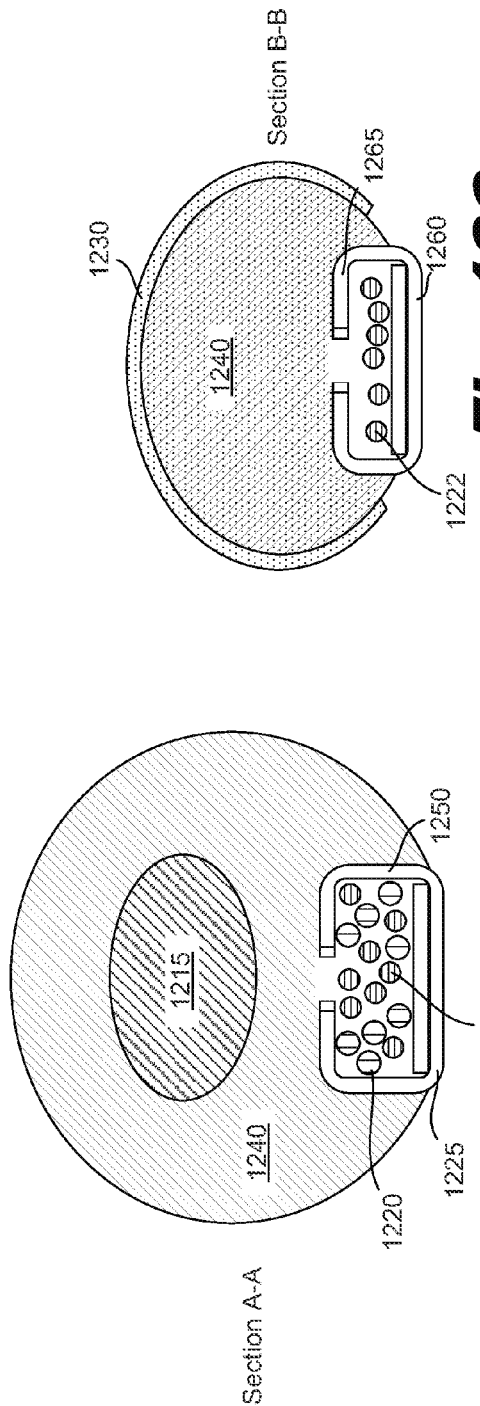

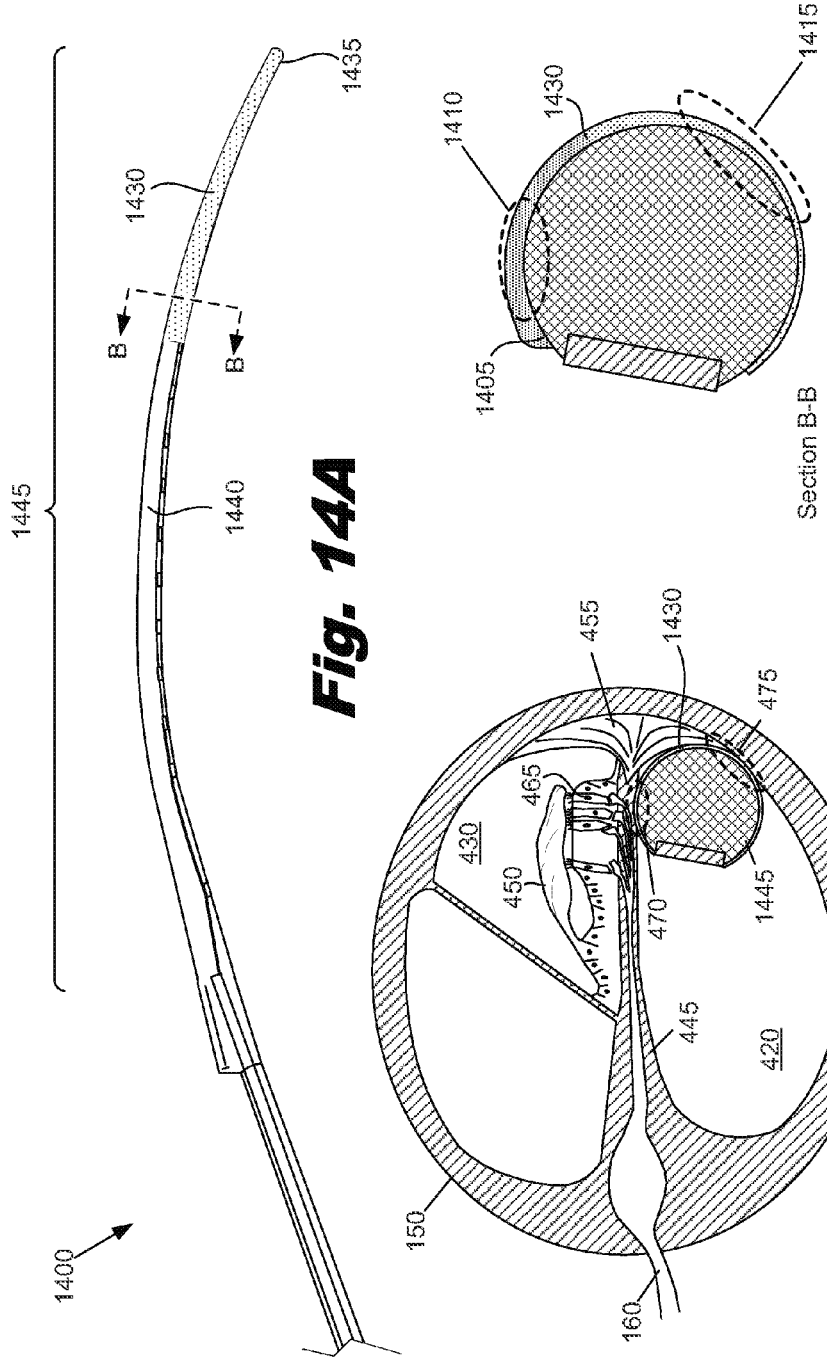

COCHLEAR ELECTRODE ARRAY

BACKGROUND

In human hearing, hair cells in the cochlea respond to sound waves and produce corresponding auditory nerve impulses. These nerve impulses are then conducted to the brain and perceived as sound.

Hearing loss, which may be due to many different causes, is generally of two types: conductive and sensorineural. Conductive hearing loss typically occurs where the normal mechanical pathways for sound to reach the hair cells in the cochlea are impeded, for example, from damage to the ossicles. Conductive hearing loss may often be helped by using conventional hearing aids that amplify sounds so that acoustic information can reach the cochlea and the hair cells. Some types of conductive hearing loss are also treatable by surgical procedures.

Many people who are profoundly deaf, however, have sensorineural hearing loss. This type of hearing loss can arise from the absence or the destruction of the hair cells in the cochlea which then no longer transduce acoustic signals into auditory nerve impulses. Individuals with sensorineural hearing loss may be unable to derive significant benefit from conventional hearing aid systems alone, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural deafness, cochlear implant systems, or cochlear prostheses, have been developed that can bypass the hair cells located in the cochlea by presenting electrical stimulation directly to the auditory nerve fibers. This leads to the perception of sound in the brain and provides at least partial restoration of hearing function. Most of these cochlear prosthesis systems treat sensorineural deficit by stimulating the ganglion cells in the cochlea directly using an implanted electrode or lead that has an electrode array. Thus, a cochlear prosthesis operates by directly stimulating the auditory nerve cells, bypassing the defective cochlear hair cells that normally transduce acoustic energy into electrical activity to the connected auditory nerve cells.

Prior to stimulating the nerve cells, the electronic circuitry and the electrode array of the cochlear prosthesis separate acoustic signals into a number of parallel channels of information, each representing a narrow band of frequencies within the perceived audio spectrum. Ideally, each channel of information should be conveyed selectively to a subset of auditory nerve cells that normally transmit information about that frequency band to the brain. Those nerve cells are arranged in an orderly tonotopic sequence, from the highest frequencies at the basal end of the cochlear spiral to progressively lower frequencies towards the apex.

A cochlear implant system typically comprises both an external unit that receives and processes ambient sound waves and a cochlear implant that receives data from the external unit and uses that data to directly stimulate the auditory nerve. A cochlear implant is a surgically implanted electronic device having electrodes that reside in the cochlea of a patient's ear and provides a sense of sound to the patient who is profoundly deaf or severely hard of hearing. In a typical cochlear implant, an array of electrode contacts are placed along one side of an elongate carrier, of a lead, so that when the array is implanted within one of the cochlear ducts, such as the scala tympani, the electrode contacts are positioned in close proximity to the cells that are to be stimulated. This allows such cells to be stimulated with minimal power consumption.

Inserting the lead into the cochlea can cause mechanical damage to the delicate structures within the cochlea and subsequent immune response, leading to further loss of hearing. To maximize the benefit of the cochlear implant for the patient, a goal is to minimize any trauma or damage to these cochlear structures and to maximize the long term effectiveness of the cochlear implant.

BRIEF DESCRIPTION OF THE DRAWINGS

The accompanying drawings illustrate various embodiments of the principles described herein and are a part of the specification. The illustrated embodiments are merely examples and do not limit the scope of the claims.

FIG. 7A is a side view of an illustrative cochlear lead with an integral stiffening element, according one embodiment of principles described herein.

FIGS. 7B-7E show illustrative cross-sections of stiffening elements, according to one embodiment of principles described herein.

FIG. 10A is a top view of a patterned sheet of conductive material forming a tethered set of electrodes having integral wire carriers, according to one embodiment of principles described herein.

FIG. 12A is a side view of an illustrative cochlear lead having an integral stiffening element and wire bundles with asymmetric stiffness, according to one embodiment of principles described herein.

FIGS. 12B and 12C are cross-sectional views of an illustrative cochlear lead having an integral stiffening element and wire bundles with asymmetric stiffness, according to one embodiment of principles described herein.

FIG. 14A is a side view of an illustrative cochlear lead having differential texturing, according to one embodiment of principles described herein.

FIG. 14B is a cross-sectional view of a cochlea with a cochlear lead having differential texturing inserted into the scala tympani, according to one embodiment of principles described herein.

FIG. 14C is a cross-sectional view of a cochlear lead having differential texturing, according to one embodiment of principles described herein.

Throughout the drawings, identical reference numbers designate similar, but not necessarily identical, elements.

DETAILED DESCRIPTION

Figure 1:
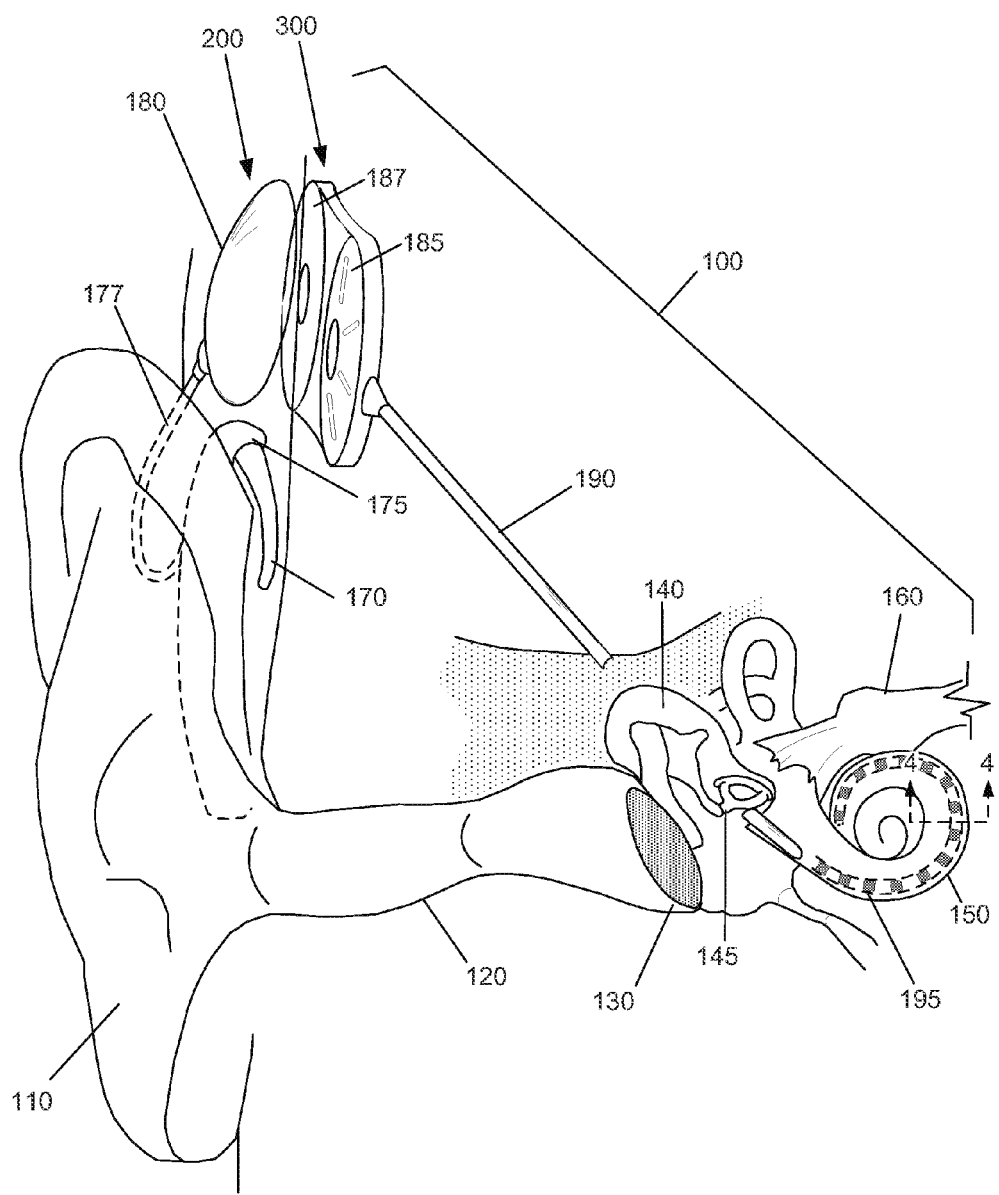
FIG. 1 is an illustrative diagram showing a cochlear implant system in use, according to one embodiment of principles described herein.

As mentioned above, individuals with hearing loss can be assisted by a number of hearing devices, including cochlear implants. To place the lead of a cochlear implant, the distal (or apical) portion of a cochlear lead is pushed through an opening into the cochlea. The distal portion of the lead is typically constructed out of biocompatible silicone, platinum-iridium wires, and platinum electrodes. This gives the distal portion of the lead the flexibility to curve around the helical interior of the cochlea. However, silicone has a high coefficient of friction and requires that a relatively high axial force be applied along the cochlear lead during the insertion process. As a result, the silicone can mechanically abrade or otherwise damage the interior of the cochlea, which can lead to further hearing loss, nerve damage, vertigo, and/or tinnitus.

As a consequence of the potential for damage to cochlea structures which results in the loss of residual hearing of a patient, the majority of patients who are considered for cochlear implants have severe or total hearing loss. For this group of patients, the benefits provided by the cochlear implant can outweigh the risk of residual hearing loss. However, by reducing the insertion trauma of the cochlear electrode array, cochlear implants could improve the hearing and quality of life of a much broader range of patients. Particularly, as a surgeon's ability to conserve residual hearing increases, the potential to implant patients with greater levels of baseline hearing can become a reality.

The initial mechanical tissue damage caused during the insertion of the cochlear lead can be significantly reduced by minimizing the size of the electrode array and by decreasing the coefficient of friction between the silicone and the body tissues. To reliably manufacture a smaller sized atraumatic electrode new processing techniques can be employed. These automated or semi-automated techniques also minimize part-to-part variability and defects which result from less controlled manual processes. The new techniques and structures described below better tailor and control the mechanical behavior of the electrode array to minimize trauma during surgical insertion. Additionally, the electrode array surfaces may be modified in order to maximize lubricity of the electrode when inserted into the cochlea. This can reduce frictional forces on the cochlea tissues, such as the basilar membrane.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "an embodiment," "an example," or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

Over the past several years, a consensus has generally emerged that the scala tympani, one of the three parallel ducts that make up the spiral-shaped cochlea, provides the best location for implantation of an electrode array used as part of a cochlear prosthesis. The electrode array to be implanted in the scala tympani typically comprises several separately connected stimulating electrode contacts, conventionally numbering about 6 to 30, longitudinally disposed on a thin, elongated, flexible carrier. Such an electrode array is pushed into the scala tympani duct in the cochlea, typically to a depth of about 1.3-30 mm via a cochleostomy or via a surgical opening made in the round window at the basal end of the duct.

In use, the cochlear electrode array delivers electrical current into the fluids and tissues immediately surrounding the individual electrode contacts to create transient potential gradients that, if sufficiently strong, cause the nearby auditory nerve fibers to generate action potentials. The auditory nerve fibers branch from cell bodies located in the spiral ganglion, which lies in the modiolus, adjacent to the inside wall of the scala tympani. The density of electrical current flowing through volume conductors such as tissues and fluids tends to be highest near the electrode contact that is the source of such current. Consequently, stimulation at one contact site tends to selectively activate those spiral ganglion cells and their auditory nerve fibers that are closest to that contact site.

FIG. 1 is a diagram showing one illustrative embodiment of a cochlear implant system (100) having a cochlear implant (300) with an electrode array that is surgically placed within the patient's cochlea. Ordinarily, sound enters the external ear, or pinna, (110) and is directed into the auditory canal (120) where the sound wave vibrates the tympanic membrane (130). The motion of the tympanic membrane is amplified and transmitted through the ossicular chain (140), which consists of three bones in the middle ear. The third bone of the ossicular chain (140), the stirrup (145), contacts the outer surface of the cochlea (150) and causes movement of the fluid within the cochlea. Cochlear hair cells respond to the fluid-borne vibration in the cochlea (150) and trigger neural electrical signals that are conducted from the cochlea to the auditory cortex by the auditory nerve (160).

As indicated above, the cochlear implant (300) is a surgically implanted electronic device that provides a sense of sound to a person who is profoundly deaf or severely hard of hearing. In many cases, deafness is caused by the absence or destruction of the hair cells in the cochlea, i.e., sensorineural hearing loss. In the absence of properly functioning hair cells, there is no way auditory nerve impulses can be directly generated from ambient sound. Thus, conventional hearing aids, which amplify external sound waves, provide no benefit to persons suffering from complete sensorineural hearing loss.

Unlike hearing aids, the cochlear implant (300) does not amplify sound, but works by directly stimulating any functioning auditory nerve cells inside the cochlea (150) with electrical impulses representing the ambient acoustic sound. Cochlear prosthesis typically involves the implantation of electrodes into the cochlea. The cochlear implant operates by direct electrical stimulation of the auditory nerve cells, bypassing the defective cochlear hair cells that normally transduce acoustic energy into electrical energy.

External components (200) of the cochlear implant system can include a Behind-The-Ear (BTE) unit (175), which contains the sound processor and has a microphone (170), a cable (177), and a transmitter (180). The microphone (170) picks up sound from the environment and converts it into electrical impulses. The sound processor within the BTE unit (175) selectively filters and manipulates the electrical impulses and sends the processed electrical signals through the cable (177) to the transmitter (180). The transmitter (180) receives the processed electrical signals from the processor and transmits them to the implanted antenna (187) by electromagnetic transmission. In some cochlear implant systems, the transmitter (180) is held in place by magnetic interaction with the underlying antenna (187).

The components of the cochlear implant (300) include an internal processor (185), an antenna (187), and a cochlear lead (190) having an electrode array (195). The internal processor (185) and antenna (187) are secured beneath the user's skin, typically above and behind the pinna (110). The antenna (187) receives signals and power from the transmitter (180). The internal processor (185) receives these signals and performs one or more operations on the signals to generate modified signals. These modified signals are then sent through the cochlear lead (190) to the electrode array (195). The electrode array (195) is implanted within the cochlea (150) and provides electrical stimulation to the auditory nerve (160).

The cochlear implant (300) stimulates different portions of the cochlea (150) according to the frequencies detected by the microphone (170), just as a normal functioning ear would experience stimulation at different portions of the cochlea depending on the frequency of sound vibrating the liquid within the cochlea (150). This allows the brain to interpret the frequency of the sound as if the hair cells of the basilar membrane were functioning properly.

Figure 2:
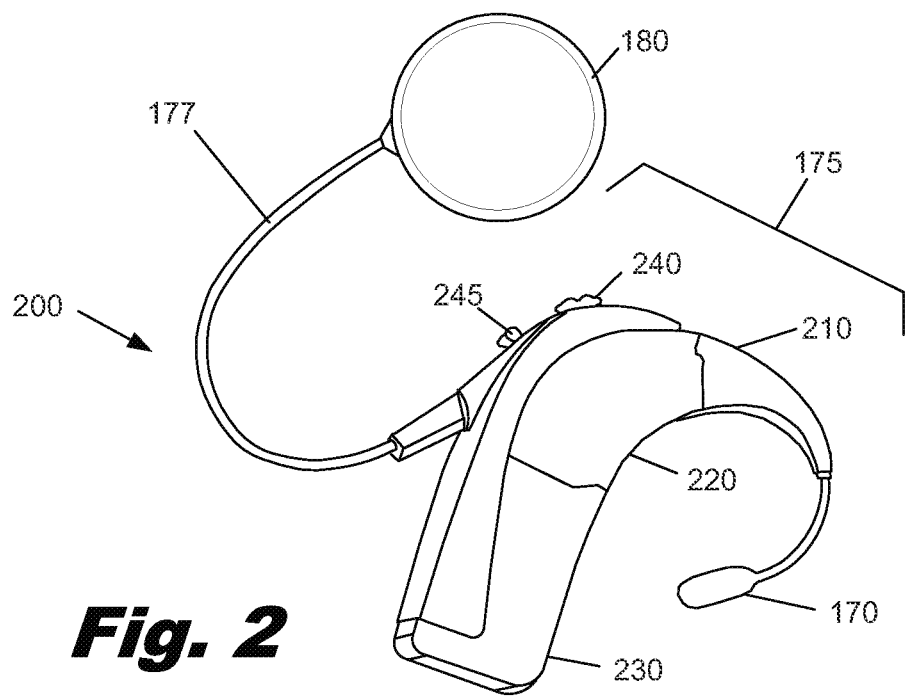
FIG. 2 is a diagram showing external components of an illustrative cochlear implant system, according to one embodiment of principles described herein.

FIG. 2 is an illustrative diagram showing a more detailed view of the external components (200) of one embodiment of a cochlear implant system. External components (200) of the cochlear implant system include a BTE unit (175), which comprises a microphone (170), an ear hook (210), a sound processor (220), and a battery (230), which may be rechargeable. The microphone (170) picks up sound from the environment and converts it into electrical impulses. The sound processor (220) selectively filters and manipulates the electrical impulses and sends the processed electrical signals through a cable (177) to the transmitter (180). A number of controls (240, 245) adjust the operation of the processor (220). These controls may include a volume switch (240) and program selection switch (245). The transmitter (180) receives the processed electrical signals from the processor (220) and transmits these electrical signals and power from the battery (230) to the cochlear implant by electromagnetic transmission.

Figure 3:
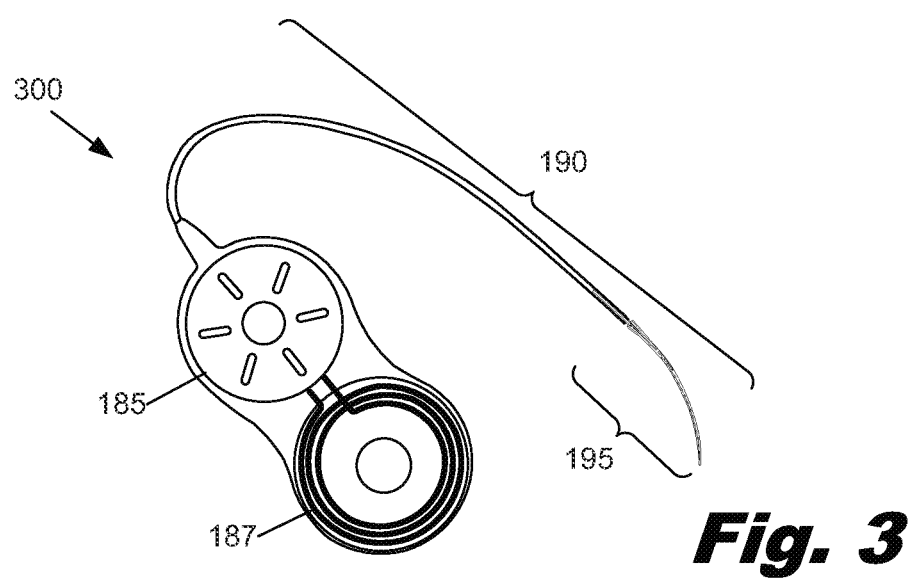
FIG. 3 is a diagram showing the internal components of an illustrative cochlear implant system, according to one embodiment of principles described herein.

FIG. 3 is an illustrative diagram showing one embodiment of a cochlear implant (300), including an internal processor (185), an antenna (187), and a cochlear lead (190) having an electrode array (195). The cochlear implant (300) is surgically implanted such that the electrode array (195) is internal to the cochlea, as shown in FIG. 1. The internal processor (185) and antenna (187) are secured beneath the user's skin, typically above and behind the pinna (110), with the cochlear lead (190) connecting the internal processor (185) to the electrode array (195) within the cochlea. As discussed above, the antenna (187) receives signals from the transmitter (180) and sends the signals to the internal processor (185). The internal processor (185) modifies the signals and passes them through the cochlear lead (190) to the electrode array (195). The electrode array (195) is inserted into the cochlea and provides electrical stimulation to the auditory nerve. This provides the user with sensory input that is a representation of external sound waves sensed by the microphone (170).

Figure 4:
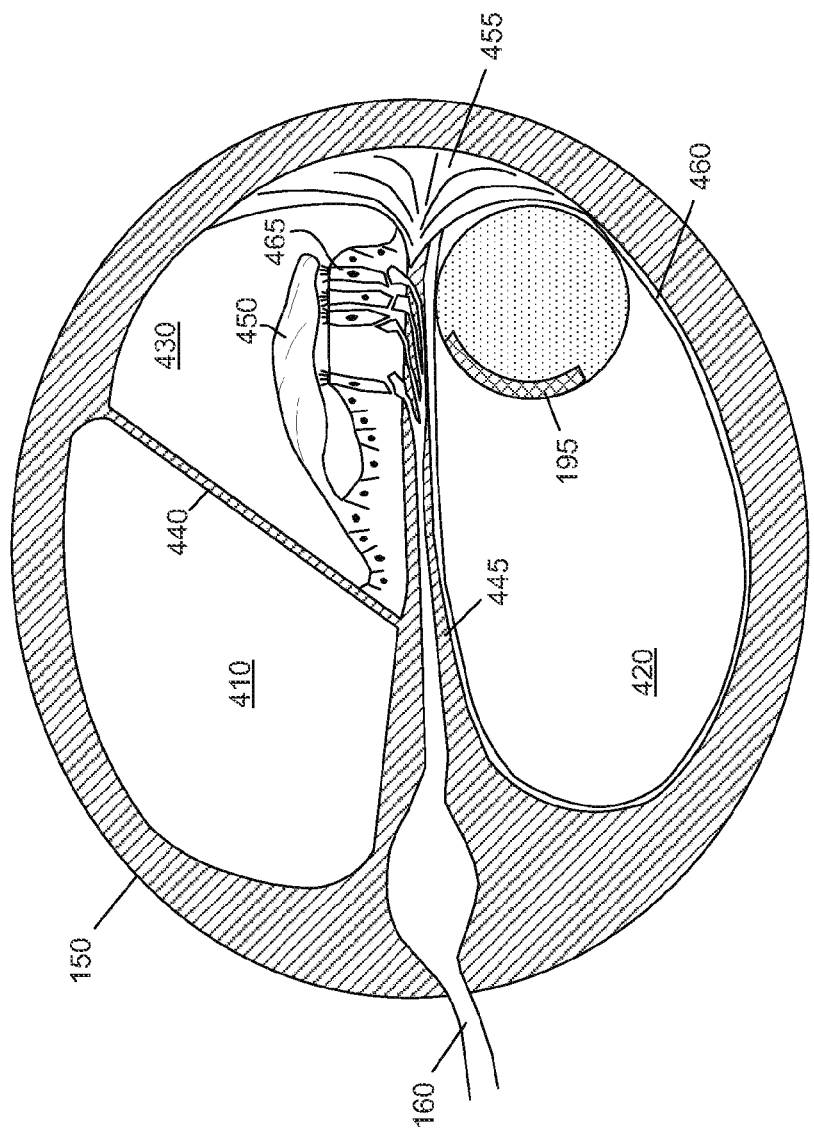
FIG. 4 is a cross-sectional view of a cochlea with an inserted electrode array, according to one embodiment of principles described herein.

FIG. 4 shows a cross sectional diagram of the cochlea (150) taken along line 4-4 in FIG. 1. The primary structure of the cochlea is a hollow, helically coiled tubular bone, similar to a nautilus shell. The coiled tube is divided through most of its length by the basilar membrane (445) and the vestibular membrane, or Reissner's membrane, (440) into three fluid-filled spaces (scalae). The scala vestibuli (410) is partitioned from the scala media (430) by Reissner's membrane (440) and lies superior to it. The scala tympani (420) is partitioned from the scala media (430) by the basilar membrane (445) and lies inferior to it. The bony walls of the cochlea are lined with a membrane, called the periosteum (460), which, in the scala media, is greatly thickened and called the spiral ligament (455). The spiral ligament (455) connects the basilar membrane (445) to the wall of the cochlea (150).

The cochlea (150) is filled with a fluid that moves in response to the vibrations coming from the middle ear via the stirrup (145). As the fluid moves, a tectorial membrane (450) and thousands of hair cells (465) in a normal, functioning cochlea are set in motion. The hair cells (465) convert that motion to electrical signals that are communicated via neurotransmitters to the auditory nerve (160), and transformed into electrical impulses known as action potentials, which are propagated to structures in the brainstem for further processing. The electrode array (195) is implanted in the cochlea, preferably within the scala tympani (420). An electrical potential is generated by the electrode, which stimulates the auditory nerve (160).

Figure 5:
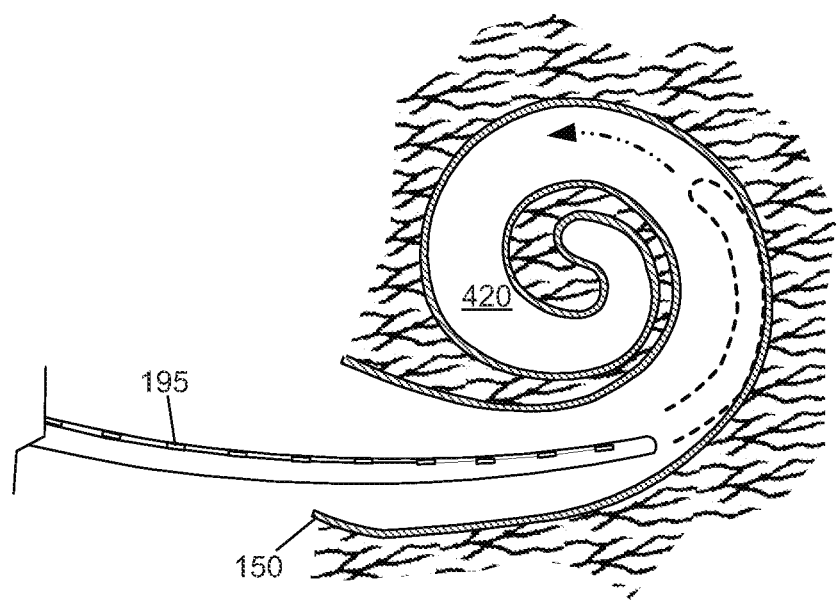
FIG. 5 is a cross-sectional view of an illustrative electrode array being inserted into a cochlear duct, according to one embodiment of principles described herein.

FIG. 5 is a cross-sectional diagram of a cochlea (150) and shows an illustrative electrode array (195) being inserted into the cochlea. A typical cochlea includes approximately two and a half helical turns of its various constituent channels. However, the cross-sectional plane shown in FIG. 5 intersects only a portion of the cochlea which contains approximately one and three quarters turns. As shown in FIG. 5, the tip of the electrode array (195) is inserted through a surgically created opening in the cochlea (150) and pushed into the scala tympani (420) so that the tip of the array conforms to the helical shape of the scala tympani. Alternatively, the electrode array (195) can be inserted through the round window of the cochlea (150). During electrode insertion there is the potential to damage the delicate structures within the cochlea. To insert the electrode array (195), a passageway is made through the bone and soft tissues of the head to expose the cochlea (150). The tip of the electrode array (195) is inserted through an opening in the cochlea. The electrode array (195) is then pushed axially into the cochlea. The force of the tip against the wall of the cochlear channel bends the flexible tip. When the tip is in its final position, the electrode array (195) is entirely contained within the cochlea and the individual electrodes lie proximate the auditory nerve (160, FIG. 4).

When electrical current is routed into an intracochlear electrode, an electric field is generated and the auditory nerve (160, FIG. 4) is stimulated.

Figure 6A:
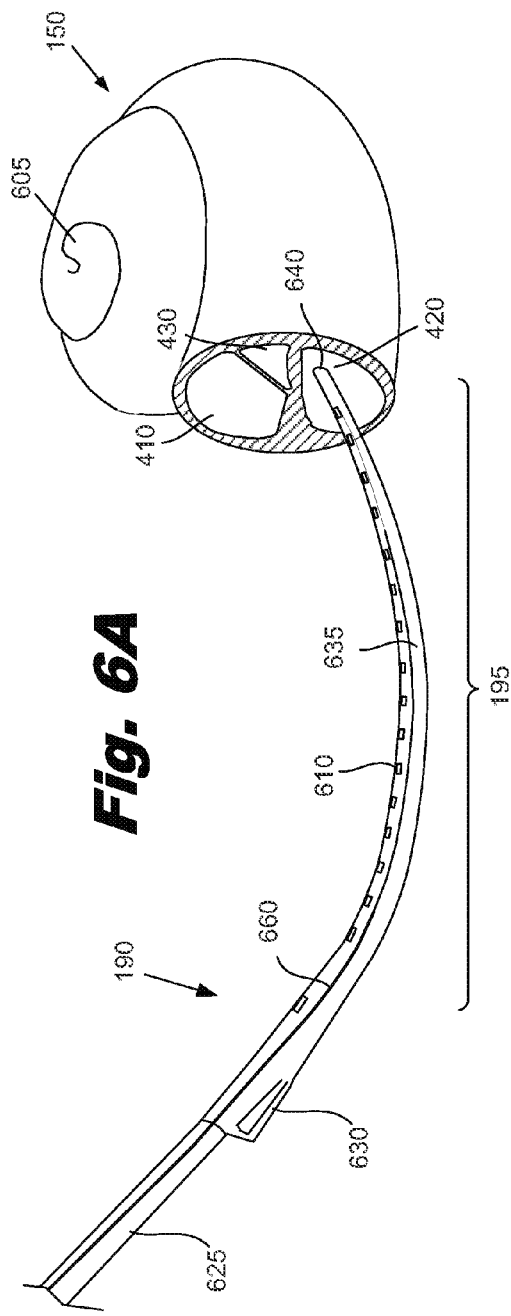
FIG. 6A is a perspective view of an illustrative electrode array being inserted into a cochlea, according to one embodiment of principles described herein.
Figure 6B:
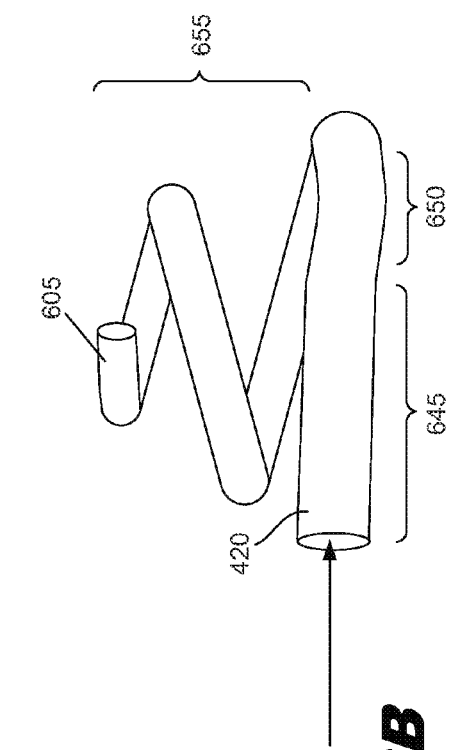
FIG. 6B is a perspective view of an illustrative three dimensional path along which an electrode array may pass during insertion into a cochlea, according to one embodiment of principles described herein.

FIG. 6A shows perspective view of an illustrative cochlear lead (190) and human cochlea (150). As previously described, the cochlea (150) is a bony structure which forms a number of channels (410, 420, 430). When viewed from the side as illustrated in FIG. 6A, these channels (410, 420, 430) are coiled in a spiral, with lower and larger coils forming the base of the spiral. The channels continue to spiral upwards with a second and smaller coil being formed on top of the first turn of the spiral. In most human cochlea, this pattern continues for two and a half turns of the cochlea and then terminates at an apex (605), where the scala tympani (420) joins the scala vestibuli (410) at the helicotrema (not shown). FIG. 6A shows only one illustrative embodiment of a human cochlea. There are normal variations in the size and structure of the cochlea. For example, when viewed from a given perspective, the left cochlea may have a clockwise spiral and a right cochlea may have a counterclockwise spiral. Where malformation or structural damage to the cochlea is a root cause hearing impairment, the cochlea may vary significantly from the illustration in FIG. 6A. Consequently, FIGS. 6A and 6B are for illustration purposes only and are not meant to be dimensionally accurate or quantitatively precise.

The illustrative cochlear lead (190) includes a lead body (625). The lead body (625) connects the electrode array (195) to the internal processor (185, FIG. 3). A number of wires (660) pass through the lead body (625) to bring electrical signals from the internal processor (185, FIG. 3) to the electrode array (195). According to one illustrative embodiment, on the lead body (625) proximal of the electrode array (195) is a molded silicone rubber feature (630). The feature (630) can serve a variety of functions, including, but not limited to, providing a structure which can be gripped by an insertion tool, providing a visual indicator of how far the cochlear lead (190) has been inserted, and securing the electrode array (195) within the cochlea.

The wires (660) that conduct electrical signals are connected to the electrodes (610) within the electrode array (195). For example, electrical signals which correspond to a low frequency sound may be communicated via a first wire to an electrode (610) near the tip (640) of the electrode array (195). Electrical signals which correspond to a high frequency sound may be communicated by a second wire to an electrode (610) near the base of the electrode array (195). According to one illustrative embodiment, there may be one wire for each electrode (610) within the electrode array (195). The internal processor (185, FIG. 3) may then control the electrical field generated by each electrode individually. For example, one electrode may be designated as a ground electrode. The remainder of the electrodes (610) may then generate electrical fields which correspond to various frequencies of sound. Additionally or alternatively, adjacent electrodes (610) may be paired, with one electrode serving as a ground and the other electrode being actively driven to produce the desired electrical field.

According to one illustrative embodiment, the wires (660) and portions of the electrodes (610) are encased in a flexible body (635). The flexible body (635) may be formed from a variety of biocompatible materials, including, but not limited to medical grade silicone rubber. The flexible body (635) secures and protects the wires and electrodes (610). The flexible body (635) allows the electrode array (195) to conform to the geometry of the cochlea.

FIG. 6B shows an illustrative three dimensional path through which the cochlear lead (190, FIG. 6A) may travel as it is inserted into the cochlea (150, FIG. 6A). Both the geometry and dimensions discussed below can vary from individual to individual, or even between left and right cochlea in the same individual.

According to one illustrative embodiment, the tip (640) of the electrode array (195) is inserted through an opening into the scala tympani (420, FIG. 6A), which is illustrated as a coiled tube. Generally, the scala tympani (420) includes a fairly straight portion (645) with a length of about four to eight millimeters. Following the straight portion (645), there may be a slight dip as the scala tympani (420) forms the base turn (650) of the spiral (655). The upward inclination of the spiral (655) may remain generally constant or may vary through successive turns. The turns become progressively tighter as the scala tympani (420) continues up the spiral (655). The spiral (655) generally terminates at the apex (605) after about two and a half turns.

The depth of insertion of the electrode array (195) into the cochlea (150) can vary, depending on the lead design, the patient's anatomy and needs, and physician technique. For example, some electrode arrays (195) may only be inserted into the relatively straight base portions of the cochlea, while other electrode arrays (195) may be inserted through one and a half rotations of the cochlea (150). Electrode arrays (195) with deeper insertions bring electrodes into close proximity to deeper spiral ganglion neurons, specifically those responsible for sensing lower frequency sounds. However, deeper insertions can also generate higher insertion forces because a larger surface area of the flexible body (635) may come into contact with the surfaces of the scala tympani (420). Additionally, as the electrode array (195) follows the scala tympani (420), contact with the interior of the cochlea may be used to conform the electrode array (195) into the spiral shape.

According to one illustrative embodiment, it is desirable that the electrode array (195) be flexible and have a low friction surface. A more flexible and low friction electrode array (195) may require less insertion force. However, it is also desirable that the electrode array (195) be stiff enough to avoid buckling during the insertion. Because the electrode array (195) is inserted from the base, an electrode array (195) that is too flexible can be difficult to push into the cochlea (150). As the electrode array (195) is progressively inserted into the cochlea (150) the insertion forces may increase. If the electrode array is too flexible, the electrode array may buckle. After buckling, the electrode array (195) may not be able to effectively transmit the insertion forces to the tip (640) of the electrode array (195) and the motion of the tip may stop. If insertion is continued after buckling, the electrode array (195) may be damaged and injury to the cochlea (150) internal structures may be caused. Consequently, it is desirable that the compliance of the electrode array (195) be carefully controlled along its length. The overall stiffness of the electrode array (195) may be controlled in a variety of ways including changing the elastic modulus of the wires, changing the diameter of the wires, changing the electrode size, changing the geometry of the silicone carrier, or changing the elastic modulus of the elastomer overmolding material.

Frictional forces may be dependent on at least two factors: the normal force from the electrode array (195) on the cochlear tissues and the coefficient of friction between the electrode array (195) and the cochlear tissues. In some embodiments, there may be a higher compliance in the apical portion of the electrode array (195), where the electrode array curves around the cochlear helix. This can reduce frictional forces because the higher compliance results in less strain energy at a given displacement, which means electrode exerts lower normal forces on the cochlea.

Although a single type of electrode array is illustrated throughout the specification and drawings, a variety of electrode array designs could incorporate the teachings of the present specification. For example, in its relaxed condition outside the body, unsupported by a stylet and unconstrained by the cochlea, the electrode array may be straight, such as that described in U.S. Pat. Nos. 6,757,970 and 7,047,081; curved, as described in U.S. Pat. No. 7,315,763; or spiral shaped, such as described in U.S. Pat. Nos. 6,604,283; 6,125,302; 7,319,906; and U.S. Publication 2008/0027527, all of which are incorporated herein by reference.

Additionally or alternatively, a discrete stiffening element may be incorporated into the electrode array (195). FIG. 7A shows one illustrative embodiment of a cochlear lead (700) that includes a stiffening element (705) in a base portion of the electrode array (195). As discussed above, an insertion tool may grip the cochlear lead (700) at or near the molded silicone rubber feature (630). According to one illustrative embodiment, the stiffening element (705) may extend from the molded silicone rubber feature (630) through a portion of the electrode array (195). The stiffening element (705) can prevent the buckling of the base portion of the electrode array (195) and make the cochlear lead (700) more responsive to surgical manipulation. According to one illustrative embodiment, the stiffening element (705) may extend through portions of the electrode array (195) which will reside in the straight portion (645, FIG. 6B) of the scala tympani (420) when the electrode array is completely inserted. In some embodiments, the stiffening element (705) may continue beyond these relatively straight regions and into the base turn of the spiral (650, FIG. 6B). According to one illustrative embodiment, the stiffening element (705) may be tapered and have progressively lower stiffness along its length.

The stiffening element may have a variety of cross-sectional geometries. FIGS. 7B through 7E show several illustrative cross-sections (710, 715, 720) that could be incorporated into the stiffening element (705). According to one illustrative embodiment, the stiffening element (705) may have a circular cross-section (710) as shown in FIG. 7B. The circular cross-section (710) provides approximately equal bending stiffness in all directions. The circular cross-section (710) may have several advantages, such as lower manufacturing costs, easier assembly because the axial orientation of the stiffening element is not critical; and a uniform response to surgical manipulation in all directions.

Additionally, the stiffening element may have a number of additional features such as temperature dependent stiffness or shape memory as described in a co-pending application titled "Composite Stylet" to Kurt Koester et al., U.S. application Ser. No. 12/470,990, filed on May 22, 2009, which is incorporated herein by reference.

FIG. 7C is an illustrative rectangular cross-sectional geometry (715) of a stiffening element (705). The resulting stiffener with rectangular cross-sectional geometry (715) may have asymmetric stiffness. For example, the bending stiffness of the stiffening element (705) may be significantly higher about a first axis (745) and lower about a second axis (750). This may allow the stiffening element (705) to preferentially bend around a spiral path within the cochlea while providing increased stiffness and control in an orthogonal direction. This could improve the ability of a surgeon to prevent the undesirable intrusion of the electrode array (195) into the basilar membrane (445, FIG. 4).

FIG. 7D is an illustrative elliptical cross-section (720). A stiffening element (705) that has an elliptical cross-section (720) may provide asymmetric stiffness as discussed above. FIG. 7E is a diagram of an illustrative composite cross-section which contains several layers (725, 730, 735, 740). The combination of the individual layers, the orientation of fibers within the layers, the bonding method between layers, the length of the layers and other factors provide additional variables which can be controlled to produce the desired behavior of the stiffening element (705).

A number of other factors can influence the stiffness of the electrode array (195). For example, the geometry of the electrodes and the wire bundle geometry and position can influence the bending stiffness of the electrode array (195).

Figure 8:
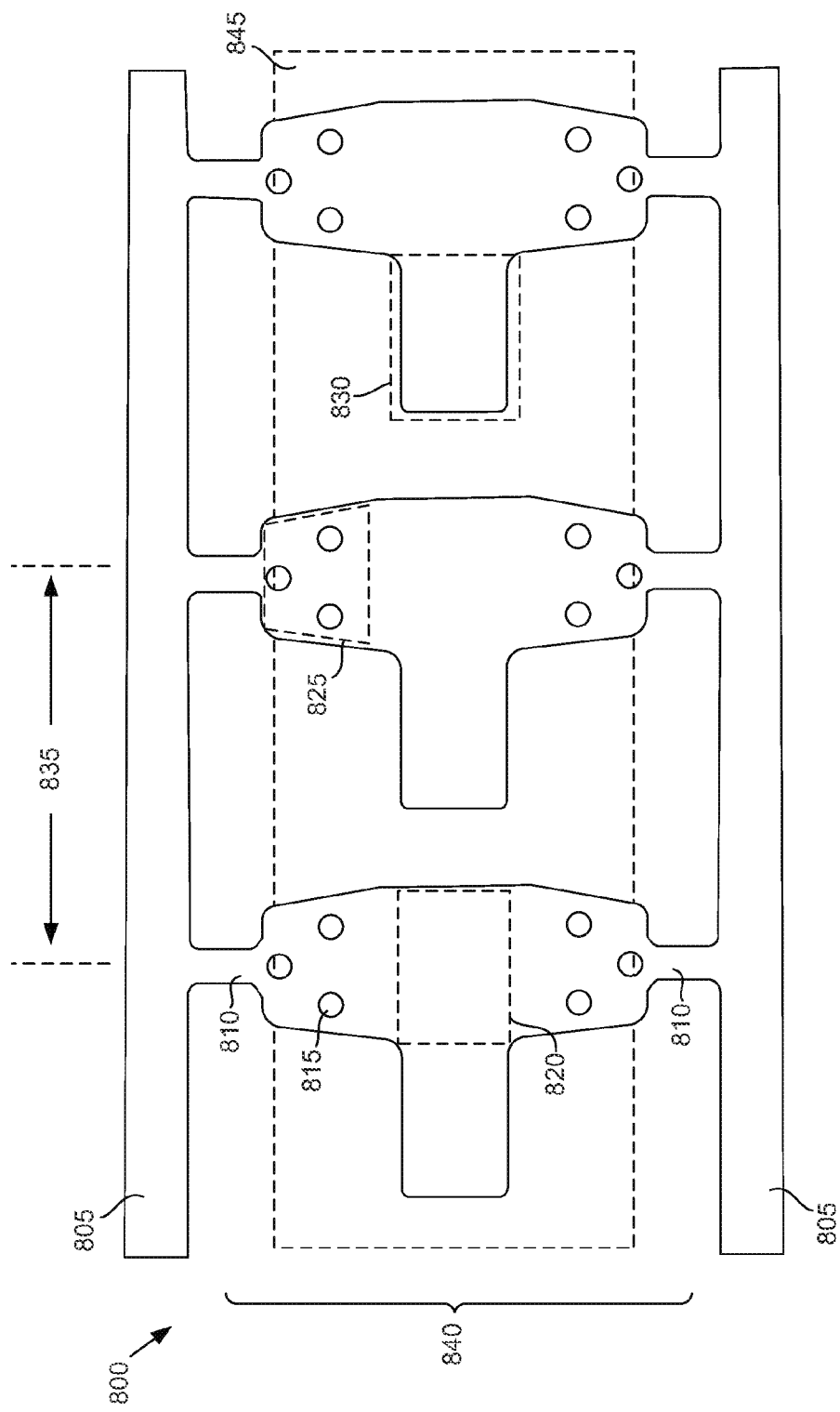
FIG. 8 is a top view of a patterned sheet of conductive material which will be used to form electrodes having integral wire carriers, according to one embodiment of principles described herein.

FIG. 8 is a diagram of an illustrative sheet of conductive material that has been cut in a preliminary step in manufacturing a cochlear lead to form a tethered set (800) of electrodes. According to one illustrative embodiment, the conductive material may be platinum. The center portions (840) of the sheet, which will later form the electrodes, are connected to a support structure formed from the same sheet. As used in the specification and appended claims, the term "support structure" refers to portions of the sheet of conductive material which hold the electrodes in substantially the same relative position in the tethered set. According to one illustrative embodiment, the support structure may be two rails (805) which are connected to the electrodes by tethers (810). As used in the specification and appended claims, the term "tether" or "tethered" refers to a connection between an electrode and the support structure which holds the electrodes in a fixed spatial relationship with other electrodes. Ordinarily, the tether has a relatively small cross-section compared to the electrode and connects between the perimeter of the electrode and the support structure. For example, the sheet material may be between 20 to 50 micron thick platinum or platinum alloy (such as platinum/iridium having up to 20% iridium). The tethers can hold the electrodes rigidly in place to completely fix the electrode spacing or semi-rigidly such they are close to their final spacing and can be put into an alignment fixture to adjust the final spacing. In one embodiment, tether widths are between 50-250 microns and lengths of the tethers are between 100-500 microns. The tether pitch, thickness, and materials are the same as the electrodes. According to one illustrative embodiment, the electrode array and tethers are formed from a single sheet of conductive material consisting of only one uniform layer.

A first dashed rectangular box outlines the portion of the center portion (840) that will become actual electrode surface (820). The dashed trapezoid illustrates portions of the geometry forming wings (825), which will be folded up to contain the wires. The wings (825) may have several additional features, such as holes (815). According to one illustrative embodiment, during a later manufacturing step, a fluid matrix such as liquid silicone rubber is injected into a mold which contains the electrodes and their associated wiring. The fluid matrix flows through the holes (815), then cures to form the flexible body (635, FIG. 6A). The holes (815) provide a closed geometry through which the fluid matrix can grip the electrode.

A second dashed rectangle outlines a flap (830), which will be folded over the wire and welded to mechanically secure it to the electrode. This wire provides electrical energy to the electrode. The spacing (835) of the electrodes as positioned along the rail (805) determines the pitch of the electrodes in the final electrode array.

According to one illustrative method, a sacrificial iron strip (845) is laid under the sheet. The sacrificial iron strip (845) is approximately the width of the electrodes and at least as long as the tethered set of electrodes (800). A spot weld is made in the area of the electrode surface (820) to secure each of the central geometries to the sacrificial iron strip (845). A thin coating of silicone or other biocompatible insulating material can be deposited over an inner surface of the electrodes and wings and cured. This silicone layer provides a compliant and electrically insulating layer between the wires and the electrodes. The silicone layer can prevent mechanical abrasion and/or electrical shorting of the wires. According to one illustrative embodiment, the wires are also individually insulated. For example, the wires may be individually insulated by a parylene coating. The tethers (810) are then cut and the tethers and rails (805) are removed. The individual wires are laid in place over their respective electrodes. The flap (830) is then folded over the wire and welded to electrically and mechanically secure the electrode to the wire and to provide additional mechanical support for the connection. The wires from each electrode are placed over the center portion of the preceding electrode. The wings (825) are folded up to secure the wires in place. After all the wires are in place the sacrificial iron strip is chemically removed, leaving integral wire carriers formed around the wire bundle. According to one illustrative embodiment, this wiring assembly is then inserted into a mold and a liquid injection molding process is used to form the flexible body around the wiring assembly. In some embodiments, a stiffening element (705, FIG. 7) may also be placed in the mold prior to the molding process. The stiffening element (705) is thereby incorporated within the flexible body of the electrode array.

Figure 9A:
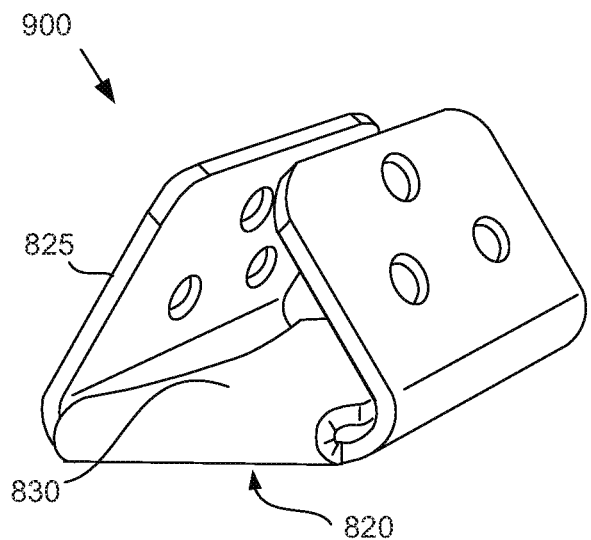
FIGS. 9A and 9B are a perspective and cross-sectional view, respectively, of one illustrative embodiment of an electrode having an integral wire carrier, according to one embodiment of principles described herein.

FIG. 9A is a perspective view of one illustrative embodiment of an electrode (900) forming an integral wire carrier. For clarity of illustration, the wires are not shown in this figure. As discussed above, the flap (830) is folded over the wire associated with this electrode (900) and welded to electrically and mechanically secure it in place. The wings (825) are folded up to secure the wires for the more distal electrodes and form a bundle of wires which passes back along the electrode array, along the cochlear lead and to the integral processor. The electrode surface (820) is on the underside of the electrode (900). The electrode surface (820) is not covered by the flexible body and is consequently exposed to the body tissues and fluids within the cochlea. The electrode surface (820) is used to generate an electrical field through these tissues, thereby stimulating the adjacent auditory nerve.

Figure 9B:
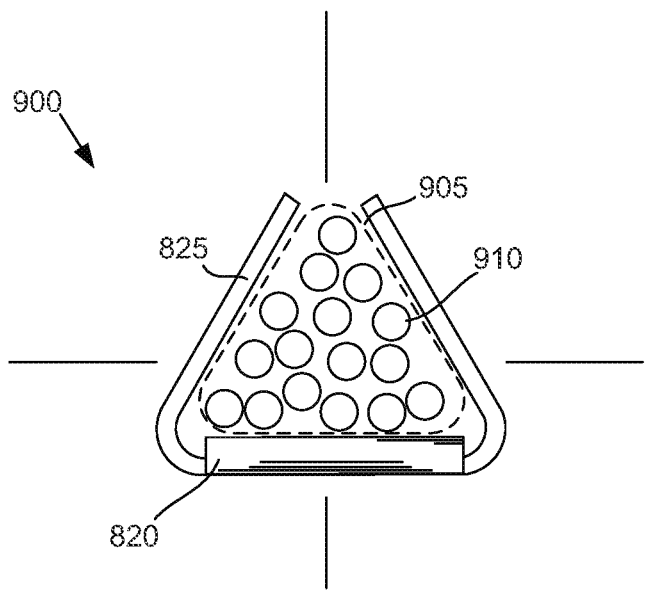

FIG. 9B is a cross-sectional view of the electrode (900) shown in FIG. 9A. Cross-sections of the wires (910) are shown in a wire bundle (905) contained by the wings (825). As discussed above, this wire bundle (905) passes through the entire length of the electrode array (195); however, each individual wire within the bundle terminated at the electrode to which it is welded. The characteristics of this wire bundle (905) can have an impact on the bending characteristics of the electrode array (195) throughout its length. For example, the bending stiffness of the individual wires (910) can influence the overall stiffness of the wire bundle (905). Similarly, the stiffness and adhesive strength of a material that fills the voids between the wires can influence the stiffness of the wire bundle (905). The geometry and position of the wire bundle (905) can also influence the bending stiffness of the wire bundle (905) and electrode array (195). As discussed above, it may be beneficial in some circumstances for the electrode array to have a considerably lower bending stiffness in one axis to allow for the electrode array (195) to easily bend around the spiral insertion path. Consequently, it can be desirable for a wire bundle to be formed such that the electrode array has asymmetric bending stiffness.

FIG. 10A is a top view of one illustrative embodiment of a sheet of conductive material which has been cut in a preliminary step in manufacturing an electrode array to form a tethered set (1000) of electrodes. The tethered set (1000) contains all the electrodes that will be incorporated into an electrode array with their correct spacing. For purposes of illustration, only a portion of the electrodes are shown: two electrodes (1050, 1055) at the base of the electrode array and one electrode (1060) at the tip of the electrode array. Similar to the embodiment shown in FIG. 8, the tethered set (1000) includes the electrodes (1050, 1055, 1060) which are held in place by rails (1005) and tethers (1010). The spacing (1035) between electrodes determines the final spacing of the electrodes in the electrode array. This spacing (1035) may vary along the length of the tethered set (1000).

According to one illustrative embodiment, the conductive material may be platinum. The overall size of the finished electrodes may be on the order of millimeters or less than a millimeter, with feature sizes on the order of tens to hundreds of microns. A first dashed rectangular box outlines the portion that will become the electrode surface (1020). A second dashed box outlines the wings (1025), which will be folded up to contain the wires. The geometry of the wings (1025) has been altered to facilitate the formation of a wire bundle with an asymmetric bending stiffness. The wings (1025) may have several additional features, such as holes (1015) and notches (1045). According to one illustrative embodiment, the notches (1045) facilitate a second bend in the wings (1025), which allows a rectangular wire carrier to be formed. As discussed above, a third dashed rectangle outlines a flap (1030), which will be folded over the wire and welded to electrically and mechanically secure it to the electrode.

FIG. 10A shows three illustrative electrodes (1050, 1055, 1060). The sizes of the electrodes (1050, 1055, 1060) may vary along the length of the tethered set (1000). According to one illustrative embodiment, the electrode nearest the base of the electrode array may have a larger overall structure than the electrode near the tip of the electrode array to allow the electrodes to accommodate the increasing number of wires in the wire bundle. However, the exposed stimulating electrode surface of each electrode may be the same for all of the electrodes.

Precisely machining the sheet to accurately cut the electrode forms and their features can be challenging. In order to better control the shape of the electrodes, very short pulse laser machining can be used to precisely form the desired geometry. As used in the specification and appended claims, the term "very short pulse" means pulses less than a nanosecond, such as in the femtosecond to hundreds of picosecond range. These very short pulse lasers provide superior micromachining compared with longer pulse lasers. The very short pulse lasers ablate illuminated material without significant transfer of heat to surrounding material. This allows the very short lasers to machine fine details and leaves the unablated material in essentially its original state. For example, very short pulse laser machining may be performed using a picosecond laser, at UV, visible, or IR wavelengths.

According to one illustrative embodiment, all of the electrodes for a single cochlear implant are machined from a single sheet of conductive material, such as platinum. For example, the electrodes can be machined at their desired spacing in the cochlear lead and be held in place to an outer frame by small tethers. The electrodes can be formed with a number of features which facilitate the final assembly of the cochlear lead. This precision laser machining and modular design can reduce the amount of manual work required and improve yields. The electrodes can then be folded to produce integral wire carriers. These wire carriers allow for the geometry and position of the wire bundle to be managed more precisely.

Figure 10B:
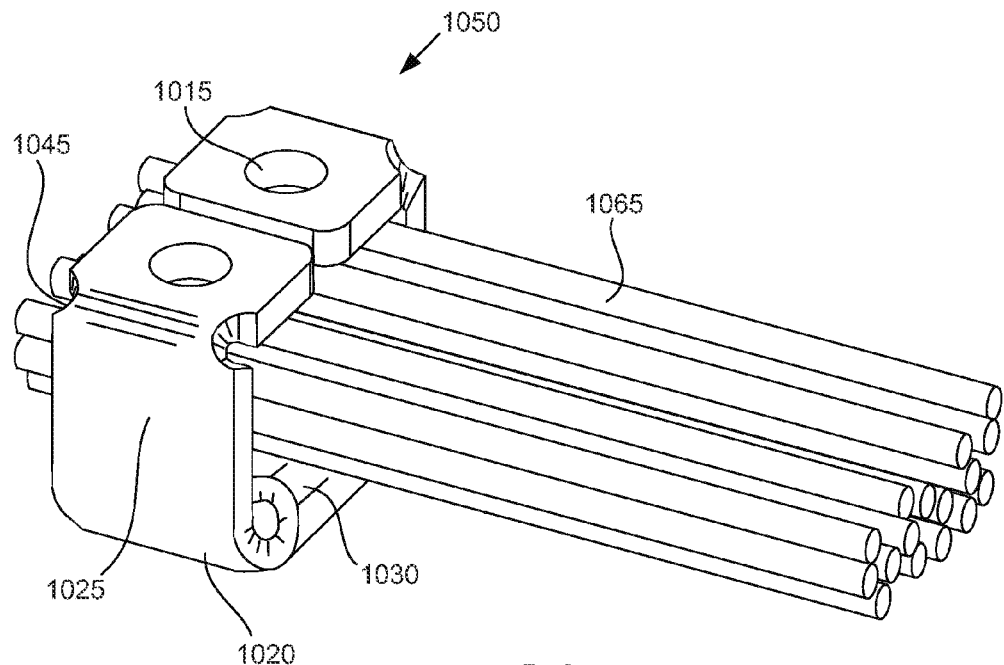
FIGS. 10B and 10C are a perspective and cross-sectional view, respectively, of one illustrative embodiment of an electrode having an integral wire carrier, according to one embodiment of principles described herein.

FIG. 10B is a perspective diagram of an illustrative electrode (1050) forming an integral wire carrier. The wings (1025) are folded twice, once near the electrode surface (1020) and again at the notches (1045) to form a rectangular wire carrier. As discussed above, the flap (1030) is folded over the wire and welded to electrically and mechanically secure it to the electrode (1050).

Figure 10C:
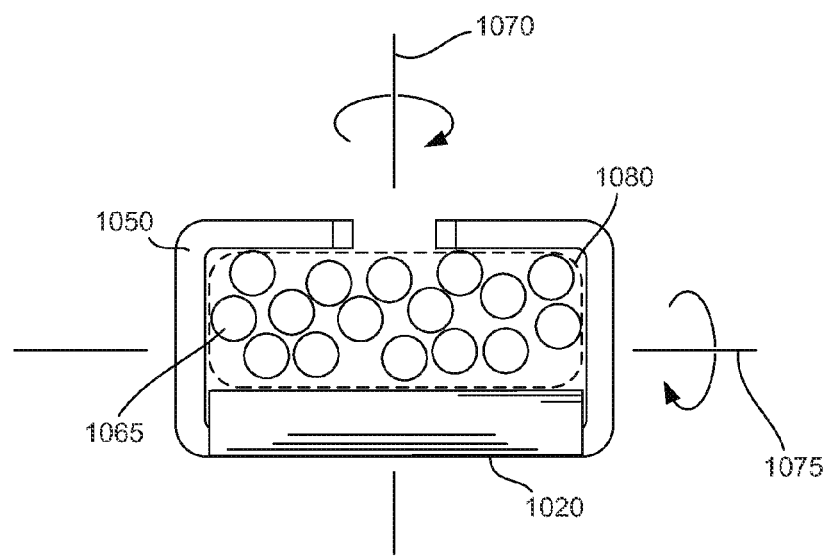

As shown in FIG. 10C, the cross section of the wire bundle (1080) is generally rectangular, with significantly higher bending stiffness about a first axis (1070) and lower stiffness about a second axis (1075). The wire bundle (1080) could be oriented so that the cochlear lead has a lower bending stiffness around the curvature of the spiral path and a higher bending stiffness in one or more other axes.

The additional accuracy provided by short pulse laser machining, allows for the more precise regulation of the position of the wire bundle and geometry of the wire bundle. This can result in more precise and desirable bending stiffnesses. The position and geometry of the wire bundle can also be controlled by using temporary spacers which are removed before molding.

Figure 11A:
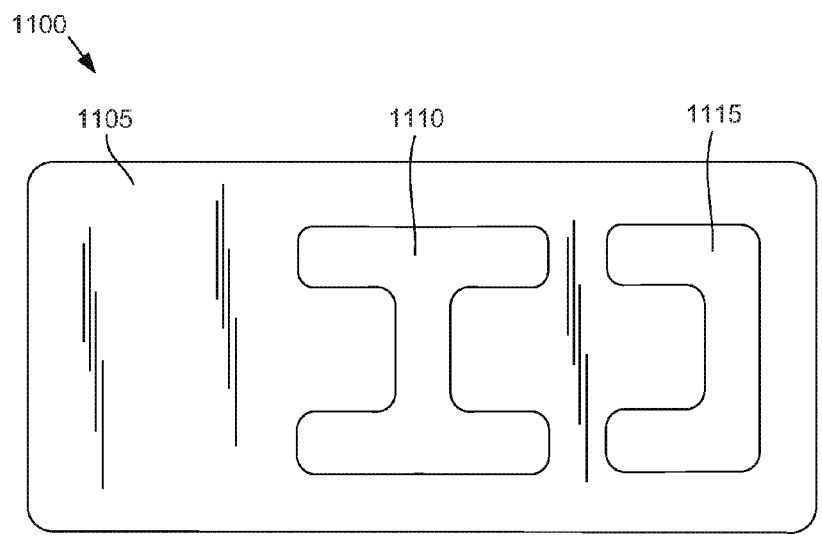
FIGS. 11A and 11B are a bottom view and perspective view of an electrode with variable flexibility over its length, according to one embodiment of principles described herein.
Figure 11B:
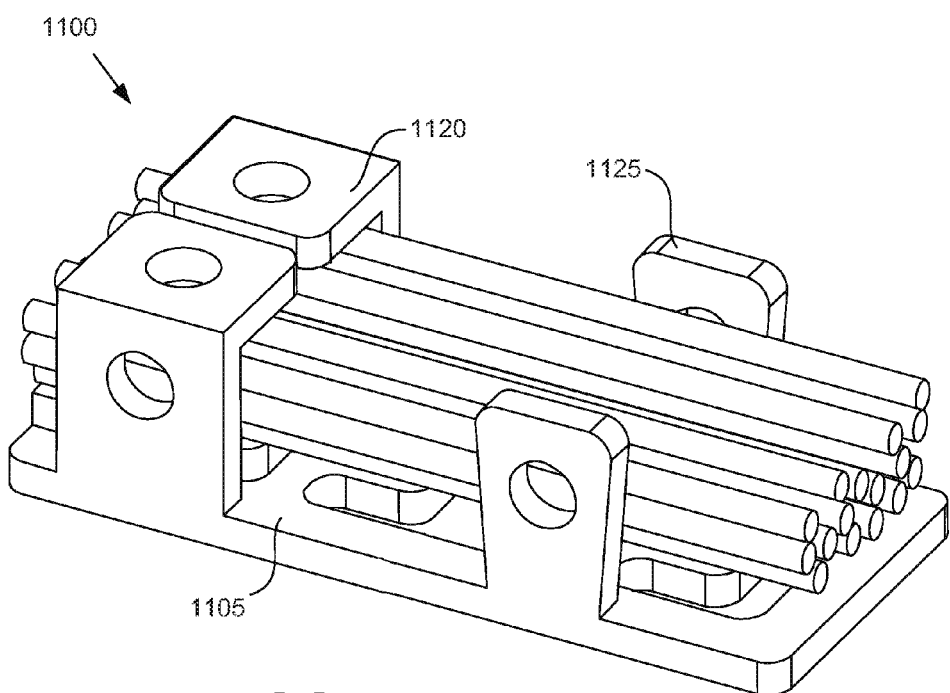

FIGS. 11A and 11B show one illustrative embodiment of an electrode (1100) having an integral wire carrier. The design of the electrode (1100) has been altered to adjust the local bending stiffness of the electrode array (195, FIG. 6). According to one illustrative embodiment, the electrode (1100) can be formed with an elongated base (1105). A number of apertures (1110, 1115) can be formed in the elongated base (1105). The apertures (1110, 1115) can be used to create varying stiffnesses along the length of the electrode base (1105) and consequently along the length of the electrode array (195, FIG. 6). In other embodiments, the stiffness of the electrode can be changed by reducing the thickness of portions of the electrode without creating apertures.

FIG. 11B shows a perspective view of the electrode (1100). A number of other features can be used to modify the stiffness of the electrode (1100). For example, the geometry of the wings (1120) can be altered to modify the stiffness of the electrode in one or more axes. Additional features, such as vertical posts (1125) may also be incorporated and have an effect on the stiffness. These posts also help anchor the electrode in the silicone.

FIGS. 12A, 12B, and 12C show one illustrative embodiment of a cochlear lead (1200) that includes a number of elements which can be tailor the bending stiffness of the lead along its length. For example, the cochlear lead (1200) incorporates a stiffening element (1215), an electrode design that creates a wire bundle with a rectangular cross-section, a flexible body (1240) with a cross-sectional geometry that varies over the length of the electrode array (1245), and varying wire sizes. Similar to the geometry described above with respect to FIG. 7A, FIG. 12A shows a lead body (1205), which connects the electrode array (1245) to the internal processor. The electrode array (1245) comprises a number of electrodes (1225), each of which is connected to one wire (1220, 1222) within a wire bundle. The wire bundle becomes much smaller toward the tip (1235) of the electrode array (1245) as wires are successively terminated at each electrode (1225).

According to one illustrative embodiment, a stiffening element (1215) is incorporated into the base portion of the electrode array (1245). The stiffening element (1215) may extend from within the lead body (1205), past the molded silicone rubber feature (1210), and down a portion of the electrode array (1245). The stiffening element (1215) can prevent the buckling of the base and make the cochlear lead (1200) more responsive to surgical manipulation. As previously discussed, the stiffening element (1215) may have various cross sectional geometries and be tapered to produce a progressively lower stiffness along its length.

FIG. 12B shows a cross sectional diagram of the electrode array (1245, FIG. 12A) along line A-A. According to one illustrative embodiment, the stiffening element (1215) has an elliptical cross-section and produces an asymmetric bending stiffness. As described above, the electrode (1225) has wings (1250) that are folded up to contain the wires (1220) and produce a wire bundle with a rectangular cross-section.

FIG. 12C shows a second cross-sectional diagram of the electrode array (1245) along line B-B. At this point in the electrode array (1245, FIG. 12A), the stiffening element (1215) is no longer present. Additionally, the electrode array (1245) may have smaller wings (1265) and/or smaller electrodes (1260) to accommodate the smaller number of wires in the electrode array and the reduced diameter of the electrode array (1245, FIG. 12A) itself.

According to one illustrative embodiment, the diameters of the wires contained within the wire bundle may have different sizes or cross-sectional geometries. For example, in FIG. 12B, the wire bundle contains larger diameter wires (1220) and smaller diameter wires (1222). In this embodiment, the large diameter wires (1220) are connected to the more basal, or proximal, electrodes and the small diameter wires (1222) are connected to the apical, or distal, electrodes. Consequently, the larger diameter wires (1220) are shorter than the small diameter wires (1222) which attach to the electrodes near the tip of the electrode array. The smaller diameter wires (1222) have a lower bending stiffness than the larger diameter wires (1220). By connecting the smaller diameter wires (1222) to electrodes near the tip of the electrode array (1245), the tip of the electrode array is more flexible. FIG. 12C shows a wire bundle at section B-B which contains only the smaller wires (1222). By way of example and not limitation, the diameter of the wires (1220, 1222) may be between 15 and 35 microns. For example, the smaller wires (1222) may be approximately 20 microns, whereas those terminating in the more proximally may be approximately 25 microns. Consequently, this configuration of wires creates radial and axial anisotropic bending stiffnesses. The radial anisotropic bending stiffness is created by the shaping the wiring bundle into a rectangular or other anisotropic cross section. The axial bending stiffness is created as each wire in the bundle progressively terminates at an electrode. Additionally, by the more distal electrodes being connected to smaller wires, the flexibility of the electrode array at the distal end is enhanced.

The flexible body (1240) of the electrode array (1245) encapsulates and protects the electrode components. According to one illustrative embodiment, the cross-sectional shape of the flexible body (1240) may change over the length of the cochlear lead to produce the desired stiffness profile. For example, FIG. 12B shows a circular cross-section at section A-A and FIG. 12C shows an elliptical cross-section at section B-B. In this embodiment, the circular cross-section could provide increased stiffness in all directions, while the elliptical cross section could produce a lower being stiffness in one direction. The circular cross-section could be helpful in providing a uniform stiffness at the base of the electrode array to prevent buckling and allow for surgical manipulation of the electrode array. The elliptical cross-section could provide a lower bending stiffness as the electrode array curves around the cochlear helix, but a high stiffness in the perpendicular direction. A variety of other shapes could be used. For example, the base of the electrode array (1245) could have a square cross-section and the apical portion of the electrode array (1245) could have a more rectangular cross-section. As used in the specification and appended claims, the terms "apical region" or "apical portion" of the electrode array refers to section of the electrode array which is closer to, and includes the distal tip of the electrode array. Similarly, the terms "basal region" or "basal portion" of the electrode array refers to the portion of the electrode array closer to the proximal end of the array.

Additionally or alternatively, the properties of the silicone rubber which makes up the flexible body can change along the length of the electrode array. For example, rubber which as a cured hardness of 70 Shore A can be used to mold the proximal portion of the array and silicone rubber which has a cured hardness of 50 Shore A could be used to mold the distal end of the array. By changing the material properties of the silicone rubber along the length of the electrode array, the stiffness and other properties of the electrode array can be altered.

The apical portion of the flexible body (1240) is shown with a textured surface (1230) that decreases friction to aid insertion, as will be described in detail below. The silicone has a textured surface (1230) on this apical portion of the flexible body (1240) to reduce friction at the distal end of the lead. This textured surface (1230) may vary along the length electrode array. In some illustrative embodiments, the electrode array (1245) may be textured along its entire length. In other embodiments, only a portion of its surface has texturing. This texturing can vary axially or circumferentially over the surface of the flexible body (1240).

FIGS. 13A-13D show an illustrative texture (1300) that can be formed over a portion of the outer surface (1310) of the flexible body (635, FIG. 6). According to one illustrative embodiment, this texture (1300) provides reduced friction between the electrode array (195, FIG. 6) and the tissues within the cochlea (150, FIG. 6). The texture may cover all or most of the outer surface of the flexible body (1240, FIG. 12). In alternative embodiments, the texture may cover only a portion of the flexible body (1240). The texture may be made up of a variety of geometries. This texture reduces the surface area of the flexible body that contacts the walls of the scala tympani, and thereby reduces the overall force to insert the electrode array (195, FIG. 6).

The texture may take the form of mounds (1305) that are 5 to 50 microns in height, 25 to 200 microns in diameter at mid-height, and have a center-to-center pitch of approximately 50-500 microns. According to one illustrative embodiment, the texture includes mounds (1305) that are 5 to 25 microns in height, 25 to 100 microns in diameter at mid-height, and have a center-to-center pitch of approximately 50-150 microns. The geometry and distribution of the surface features can change over the surface. For example, the surface features may be adjusted according to an expected bending radius at a particular location of the electrode array. For example, on a side of the surface that is expected to be in tension during the insertion due to bending, the feature height may be increased and the pitched decreased in at least one dimension. Consequently, when the electrode array (195, FIG. 6) is bent during insertion and the outer surface begins to stretch, the mounds are reduced in height and the pitch increases in at least one dimension. By compensating for this in advance, the desired surface texture can be produced after bending deformation of the electrode array (1200, FIG. 12A).

Figure 13A:
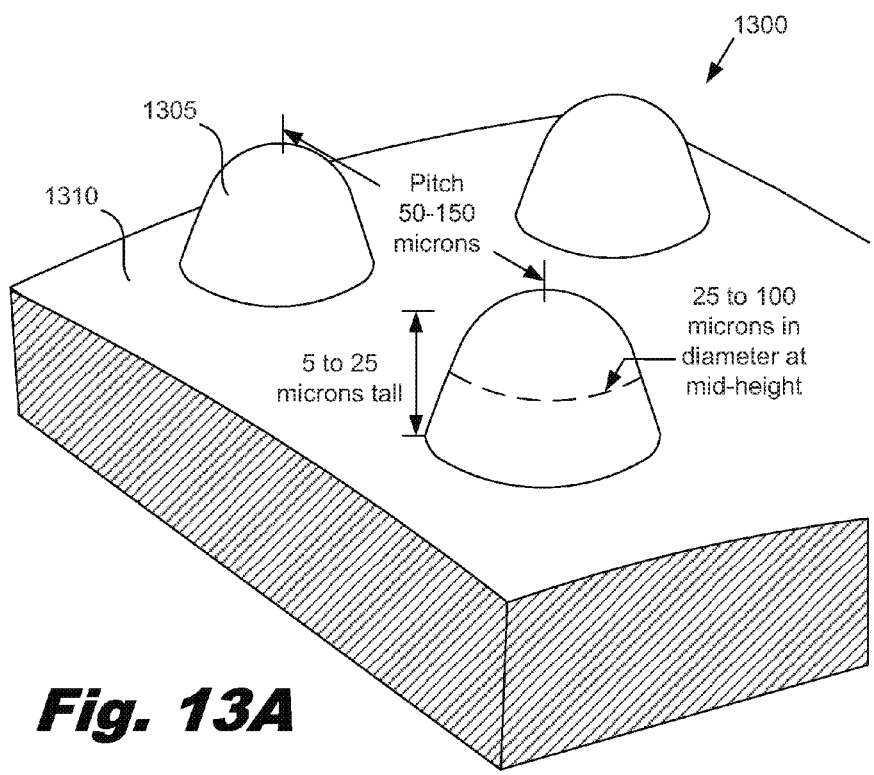
FIG. 13A is perspective view of microtexture features on the outer surface of the flexible body of an electrode array, according to one embodiment of principles described herein.
Figure 13B:
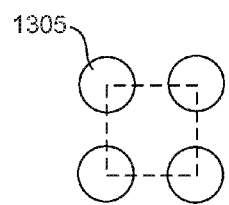
FIGS. 13B-13D are diagrams of illustrative ordered arrangements of microfeatures on an outer surface of the flexible body of an electrode array, according to one embodiment of principles described herein.
Figure 13C:
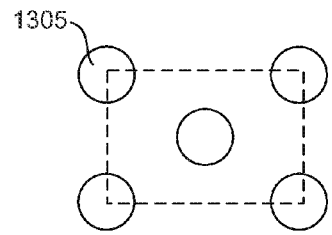
Figure 13D:
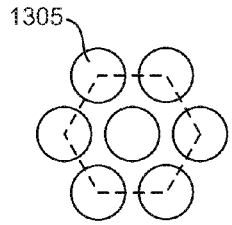

The mounds may be arranged in a variety of ordered arrays, including those shown in FIGS. 13B-D. FIG. 13B shows an illustrative square arrangement of mounds (1305), while FIG. 13C shows a rectangular arrangement with a fifth mound interposed at the center of the rectangle. FIG. 13D shows an illustrative hexagonal arrangement with a seventh mound interposed in the center of the hexagon. A variety of other arrangements could be used. These arrangements can be repeated over the surface of the flexible body and varied as required to improve the performance of the electrode array. A number of factors can influence the geometry and distribution of the surface features within the texture (1300). For example, in some cases it can be desirable to avoid certain geometries that could provide growth opportunities for bacteria or other microbes.

According to one illustrative embodiment, the ordered array of mounds (1305) are formed by machining a mold with indentations, then filling the mold with medical grade silicone. The silicone fills the indentations. After the silicone has cured, the flexible body which has an ordered array of mounds on its outer polymer surface is removed from the mold. The molding process may use a variety of techniques and molding materials, including liquid injection molding.

FIGS. 14A-14C show one illustrative embodiment of a cochlear lead (1400) that includes an electrode array (1445) with variations in surface texture, which may provide additional protection to sensitive tissues within the cochlea. The textured surface (1430) is shown as being on only a portion of the length of the flexible body (1440) of the electrode array (1445). As discussed above, the texturing may extend along all or part of the length the flexible body (1440). Furthermore, as can be more clearly seen in FIG. 14C, the surface texture varies around the perimeter of the flexible body (1440), as will be described in detail below. According to one illustrative embodiment, the flexible body (1440) has an outer polymer surface. This outer polymer surface may be a separate layer or an integral part of the flexible body. The surface texture is incorporated into this outer polymer layer.

FIG. 14B shows a cross-sectional view of the cochlea (150). As discussed above, the walls of the hollow cochlea (150) are made of bone, with a thin, delicate lining of epithelial tissue. Many of the most fragile and sensitive structures within the cochlea are attached to or located near the basilar membrane (445). These include the spiral ligament (455), tectorial membrane (450), and hair cells (465).

In some embodiments, the electrode array (1445) is inserted into the scala tympani (420). For purposes of illustration, the electrode array (1445) is shown as contacting body structures in two general body contact areas (470, 475). A first body contact area (470) includes structures above the electrode array (1445) such as the basilar membrane (445), and a second body contact area (475) includes lateral structures such as endosteum, which lines the wall of the scala tympani (420), and particularly the spiral ligament (455). A variety of factors can alter the locations of contact areas (470, 475). These factors may include cochlear variations, compliance of tissues within the cochlea, surgical variation, electrode geometries, and other factors. The contact with the exterior wall over the second body contact area (475) may not be as sensitive to sliding contact with the electrode array (1445) as the first body contact area (470) because the wall of the cochlea is relatively robust compared to the basilar membrane (445). Abrasion or puncture of the basilar membrane (445) or damage to the spiral ligament (455) joining the basilar membrane (445) to the wall of the cochlea by the electrode array can have serious consequences including a reduction in any residual hearing of the individual.

According to one illustrative embodiment, the textured surface (1430), which extends over all or a portion of the length of the flexible body (1440), may vary in structure or properties around the perimeter of the electrode to produce varying coefficients of friction around the perimeter of the electrode array. Alternatively or in combination with varying surface texture, differences in coefficients of friction around the perimeter of an electrode array may be produced by varying lubrication types, lubrication amounts, material types, material treatment like plasma or ion beam treatments, or other features. This variation in friction can be used to produce a number of beneficial effects as the electrode array is inserted into the cochlea. By way of example and not limitation, the differences in frictional forces can be altered to produce a slight, but substantial tendency for the tip (1435) of the electrode array (1445) to point downward and away from the basilar membrane (445). The various design features which alter the stiffness of the electrode array and the texturing of the surface can be combined to produce the desired motion during the insertion. It should be noted that the difference in friction, combined with the difference in flexibility of the various lead portions as discussed above, should not be so extreme as to create a tendency for the tip to fold over.

FIG. 14C shows a cross-section of one illustrative embodiment of an electrode array (1445) which has surface variations on the flexible body of the electrode array that provide different coefficients of friction around its perimeter. A first lead surface area (1410) may have lower friction than a second lead surface area (1415). This difference in friction is a relative difference between the two lead surface areas (1410, 1415). As discussed above, texturing the surface of the flexible body of an electrode array can result in a significant reduction in overall friction compared to a nontextured (essentially smooth) surface. Alternatively, a slightly different spacing or geometry of texture features could be used to create the relative difference in friction around the perimeter of the cochlear lead in the two lead surface areas (1410, 1415) generally contacting the two body contact areas (470 and 475, respectively, FIG. 14B). The resulting imbalance in frictional forces may have a tendency to point the tip (1435) of the electrode array (1445) downward and away from the basilar membrane (445) during insertion. This may reduce the tendency of the electrode array (1445) to abrade and/or puncture the basilar membrane (445), consequently preserving residual hearing of the individual.

The textures on the outer surfaces of the flexible body may be formed in a variety of ways. For example, the texture may be machined into a liquid injection mold. The silicone is then injected under pressure into the mold and fills the mold. The silicone is then allowed to cure and the mold is removed. The resulting electrode array then has the desired texture on its outer surface. A variety of other techniques could be used, including but not limited to, laser ablation of the outer surface of the electrode array, deposition of additional material after the electrode array is formed, and other suitable methods. Notice that in FIG. 14C, the change in surface features can vary gradually around the perimeter, producing a region of lower friction in a first lead surface area (1410) and a region of relatively higher friction in a second lead surface area (1415). These gradual changes in surface texture could be created by varying any of a number of design parameters including, but not limited to, the spacing of the features on the surface, the height of the features, the shape of the features, or other parameters.

Alternatively, although not shown, the change to the surface producing the frictional difference may be abrupt, creating discrete regions of lower and higher friction. This abrupt change from texturing to no texturing was illustrated in FIG. 12A with respect to axial changes, but a similar technique could be used for changes to surface texture in the radial direction around the perimeter of the lead.

In sum, a cochlear electrode array can incorporate a number of features and manufacturing techniques which reduce damage to tissues during insertion. Some of these features are directed toward improving the stiffness characteristics of the electrode array. This can improve surgical control over the electrode array during insertion, reduce the likelihood of buckling, and reduce the overall insertion force. Some of these features and manufacturing techniques are directed toward improving process control of very small parts and allowing manufacturing of leads having smaller electrode array diameters, such as less than 0.5 mm, than have heretofore been possible. For example, electrode arrays having diameters at least as small as of 0.4 mm can be manufactured using the techniques and geometries described above. The friction of the electrode array may also be reduced by forming a texture on the outer surface of the electrode array. According to one illustrative embodiment, a circumferential difference in the texture can produce a guiding force which directs the tip of the electrode array away from the basilar membrane. This can reduce damage to the sensitive structures of the basilar membrane and better preserve residual hearing. Additionally, because of the small size and reduced insertion damage, the electrode array could also be used in conjunction with electro-acoustic stimulation. For example, an electro-acoustic device such as a hearing aid may be used in conjunction with the cochlear implant to provide mechanical stimulation to functioning hair cells.

The preceding description has been presented only to illustrate and describe embodiments and examples of the principles described. This description is not intended to be exhaustive or to limit these principles to any precise form disclosed. Many modifications and variations are possible in light of the above teaching.

What is claimed is:

1. A cochlear lead comprising:
  a plurality of electrodes configured to stimulate an auditory nerve from within a cochlea; and
  a flexible body supporting said plurality of electrodes, said flexible body having an outer surface comprising:
    a first region configured to produce a lower coefficient of friction when said cochlear lead is inserted into a cochlear duct; and
    a second region configured to produce a higher coefficient of friction when said cochlear lead is inserted into the cochlear duct, wherein said first region is positioned to be more proximate to a basilar membrane than said second region when said cochlear lead is inserted into the cochlear duct;
    wherein said lower coefficient of friction of said first region and said higher coefficient of friction of said second region produce a differential sliding force to move a tip of said cochlear lead away from the basilar membrane.

2. The cochlear lead of claim 1, wherein said outer surface comprises a surface texture configured to contact a wall of a cochlear duct, wherein said surface texture varies about a circumference of said flexible body, thereby forming said first region, second region and differential sliding force.

3. The cochlear lead of claim 1, wherein said outer surface comprises one or more lubricants such that varying coefficients of friction are produced about a circumference of said flexible body.

4. The cochlear lead of claim 1, in which said first and second regions comprise an ordered array of mound shaped features approximately 5 to 25 microns in height, with a diameter of approximately 25 to 100 microns and a spacing between said features of approximately 50 to 150 microns.

5. The cochlear lead of claim 4, in which said flexible body comprises molded silicone, in which said ordered array of mound shaped features are molded textures on said outer surface of said cochlear lead.

6. The cochlear lead of claim 1, in which a surface texture on said outer surface of said flexible body changes gradually between said first region and said second region.

7. The cochlear lead of claim 1, in which material forming said flexible body has a hardness which varies along a length of said flexible body.

8. The cochlear lead of claim 1, wherein said plurality of electrodes are spaced apart along said cochlear lead between a proximal end and a distal end; and
said cochlear lead further comprises a plurality of wires, comprising:
a first wire having a first diameter and electrically coupled to a first electrode of said plurality of electrodes; and
a second wire having a second diameter less than said first diameter and electrically coupled to a second electrode of said plurality of electrodes distal of said first electrode.

9. The cochlear lead of claim 8, in which said plurality of wires is formed into a wire bundle, said wire bundle having radial and axial anisotropic bending stiffnesses.

10. The cochlear lead of claim 8, further comprising a stiffening element, said stiffening element extending only partway into said cochlear lead.

11. The cochlear lead of claim 8, wherein said flexible body comprises a proximal cross-sectional geometry and a distal cross-sectional geometry, in which said proximal cross-sectional geometry is configured to have a more radially symmetric and higher bending stiffness than said distal cross-sectional geometry.

12. The cochlear lead of claim 8, wherein said cochlear lead has a diameter of less than 0.5 millimeters.

13. The cochlear lead of claim 1, wherein said outer surface comprises a first side to be in tension during insertion of said cochlear lead into a cochlea and a second side of said outer surface to be in compression during insertion of said cochlear lead into said cochlea, wherein features on said first side comprise higher feature height than features on said second side when said cochlear lead is in a relaxed condition outside the cochlea.

14. The cochlear lead of claim 13, wherein said features on said first side of said outer surface comprises a smaller pitch between features than features on said second side of said outer surface when said cochlear lead is in a relaxed condition outside the cochlea.

15. A cochlear lead comprising:
a plurality of electrodes configured to stimulate an auditory nerve from within a cochlea; and
a flexible body supporting said plurality of electrodes, said flexible body comprising an outer surface to contact a wall of a cochlear duct, said outer surface comprising surface features distributed around a circumference of said flexible body;
wherein when said cochlear lead is in a relaxed condition outside the cochlea, a first side of said outer surface to be in tension during insertion of said cochlear lead into the cochlea comprises higher feature height and decreased pitch between features than features on a second side of said outer surface to be in compression during insertion of said cochlear lead into the cochlea.

16. The cochlear lead of claim 15, wherein during insertion of said cochlear lead into a cochlea, bending of said cochlear lead stretches said first side of said outer surface thereby reducing feature height and increasing pitch between features on said first side.

17. The cochlear lead of claim 16, wherein geometry and distribution of surface features changes over said surface.

18. A cochlear lead comprising:
a plurality of electrodes configured to stimulate an auditory nerve from within a cochlea; and
a flexible body supporting said plurality of electrodes, said flexible body comprising an outer surface comprising:
a first region having a first coefficient of friction: and
a second region having a second and different coefficient of friction, wherein said first region contacts a basilar membrane and said second region is more distal from said basilar membrane to create a differential sliding force configured to direct a tip of said cochlear lead away from a basilar membrane during insertion of said cochlear lead into the cochlea.

19. The cochlear lead of claim 18, wherein said second region is configured to contact an endosteum and spiral ligament on a lateral wall of a scala tympani duct of the cochlea, wherein said first region has a low coefficient of friction and said second region has a higher coefficient of friction.

20. The cochlear lead of claim 18, in which said second region is on a side of said cochlear lead opposite said electrodes and said first region of said outer surface is between said electrodes and said second region.

* * * * *